United States Patent [19]
Adamczyk et al.

[11] Patent Number: 5,459,080
[45] Date of Patent: * Oct. 17, 1995

[54] ION-CAPTURE ASSAYS USING A SPECIFIC BINDING MEMBER CONJUGATED TO CARBOXYMETHYLAMYLOSE

[75] Inventors: Janina Adamczyk, Gurnee; Daniel S. Berry, Libertyville; Yi-Her Jou, Libertyville; Stephen D. Stroupe, Libertyville, all of Ill.

[73] Assignee: Abbott Laboratories, Abbott Park, Ill.

[*] Notice: The portion of the term of this patent subsequent to Jan. 27, 2014 has been disclaimed.

[21] Appl. No.: 187,814

[22] Filed: Jan. 27, 1994

Related U.S. Application Data

[63] Continuation of Ser. No. 707,726, May 30, 1991, abandoned, which is a continuation-in-part of Ser. No. 375,029, Jul. 7, 1989, abandoned, which is a continuation-in-part of Ser. No. 150,278, Jan. 29, 1988, abandoned.

[51] Int. Cl.$^6$ .......... G01N 33/544; G01N 33/532; G01N 33/538
[52] U.S. Cl. .......... 436/538; 436/539; 436/541; 436/544; 436/528; 435/7.92; 435/7.93; 435/7.94; 435/961
[58] Field of Search ............ 436/518, 528, 436/536, 538, 539, 177; 435/7.1, 7.92, 7.93, 962, 971

[56] References Cited

U.S. PATENT DOCUMENTS

| | | | |
|---|---|---|---|
| 4,020,151 | 4/1977 | Bolz et al. | 436/527 |
| 4,104,026 | 8/1978 | Brooker et al. | 436/541 |
| 4,121,975 | 10/1978 | Ullman et al. | 435/7.9 |
| 4,144,306 | 3/1979 | Figueras | 422/56 |
| 4,145,406 | 3/1979 | Schick et al. | 436/541 |
| 4,180,383 | 12/1979 | Johnson | 422/69 |
| 4,278,651 | 7/1981 | Hales | 436/532 |
| 4,298,685 | 11/1981 | Parikh et al. | 435/7.5 |
| 4,343,896 | 8/1982 | Wolters et al. | 435/5 |
| 4,362,697 | 12/1982 | Tabb et al. | 422/56 |
| 4,501,692 | 2/1985 | Gibbons et al. | 530/391.5 |
| 4,517,288 | 5/1985 | Giegel et al. | 435/5 |
| 4,530,900 | 7/1985 | Marshall | 435/7.5 |
| 4,624,930 | 11/1986 | Tanswell et al. | 435/5 |
| 4,632,901 | 12/1986 | Valkirs et al. | 435/5 |
| 4,672,045 | 6/1987 | Tsutsui et al. | 436/518 |
| 4,673,734 | 6/1987 | Tayot et al. | 530/364 |
| 4,727,019 | 2/1988 | Valkirs et al. | 435/5 |
| 4,740,468 | 4/1988 | Weng et al. | 435/7.91 |
| 4,780,409 | 10/1988 | Monji et al. | 435/7.36 |
| 4,806,311 | 2/1989 | Greenquist | 422/56 |
| 4,839,231 | 6/1989 | Vandekerckhove | 428/441 |
| 4,868,108 | 9/1989 | Bahar et al. | 435/7.92 |
| 4,880,751 | 11/1989 | Georghegan | 436/518 |
| 4,935,147 | 6/1990 | Ullman et al. | 210/695 |
| 4,943,522 | 7/1990 | Eisenger et al. | 435/7.25 |
| 4,948,726 | 8/1990 | Longoria | 435/7.5 |
| 4,956,275 | 9/1990 | Zuk et al. | 435/7.92 |
| 4,959,303 | 9/1990 | Milburn et al. | 435/7.36 |
| 4,959,307 | 9/1990 | Olson | 435/7.91 |
| 5,051,356 | 9/1991 | Warren, III et al. | 435/7.34 |
| 5,075,220 | 12/1991 | Pronovost | 435/7.36 |
| 5,094,962 | 3/1992 | Snyder et al. | 436/518 |

FOREIGN PATENT DOCUMENTS

| | | |
|---|---|---|
| 160900 | 11/1985 | European Pat. Off. . |
| 214909 | 3/1987 | European Pat. Off. . |
| 230768 | 8/1987 | European Pat. Off. . |
| 299428 | 1/1989 | European Pat. Off. . |
| 8402193 | 6/1984 | WIPO . |
| 89/06791 | 7/1989 | WIPO . |

OTHER PUBLICATIONS

Aebersold et al, *J. Biol. Chem.*, 261:4229–4238 (1986).
Chernesky et al., *J. Clin. Micro.*, 20:400–404 (1984).
Hewick et al., *J. Biol. Chem.*, 256:7990–7996 (1981).
Liu et al., *Biochem.*, 18:690–696 (1979).
Meares et al., *Anal. Biochem.*, 142:68–78 (1984).
Tsukada et al., *JNCL*, 73:721–728 (1984).

*Primary Examiner*—Toni R. Scheiner
*Assistant Examiner*—Nancy J. Parsons

[57] ABSTRACT

The present invention includes novel assays employing a capture reagent, involving a first specific binding member conjugated to a polymeric anion such as carboxymethylamylose, and a solid phase material containing a reaction site comprising a polymeric cation substance. A test sample suspected of containing the analyte of interest may be contacted with the capture reagent to form a charged capture reagent/analyte complex. The complex is then contacted to/ the oppositely charged solid phase to attract, attach, and immobilize the capture reagent/analyte complex. The use of carboxymethylamylose to prepare a suitably charged capture reagent provides a superior capture reagent that is capable of binding and retaining the analyte on the solid phase even in the presence of polyanionic non-specific binding blockers.

11 Claims, No Drawings

ION-CAPTURE ASSAYS USING A SPECIFIC BINDING MEMBER CONJUGATED TO CARBOXYMETHYLAMYLOSE

This application is a continuation of application Ser. No. 07/707,726, filed May 30, 1991, abandoned, which is a continuation-in-part of U.S. application Ser. No. 375,029, filed Jul. 7, 1989, now abandoned which is a continuation-in-part of U.S. application Ser. No. 150,278, filed January 29, 1988 now abandoned.

BACKGROUND OF THE INVENTION

1. Field of the Invention

This invention relates generally to the field of binding assay devices and methods. In particular, the present invention relates to novel devices useful in the performance of homogeneous immunoassays.

2. Description of Related Art

Various analytical procedures and devices are commonly employed in assays to determine the presence and/or concentration of substances of interest or clinical significance which may be present in biological liquids or other materials. Such substances are commonly termed "analytes" and can include antibodies, antigens, drugs, hormones, etc.

Immunoassay techniques take advantage of the mechanisms of the immune systems of higher organisms, wherein antibodies are produced in response to the presence of antigens which are pathogenic or foreign to the organisms. These antibodies and antigens, i.e., immunoreactants, are capable of binding with one another, thereby creating a highly specific reaction mechanism which can be used in vitro to determine the presence or concentration of that particular antigen in a biological sample.

There are several known immunoassay methods using immunoreactants, wherein at least one of the immunoreactants is labeled with a detectable component so as to be analytically identifiable. For example, the "sandwich" or "two-site" technique may involve the formation of a ternary complex between an antigen and two antibodies. A convenient method of detecting complex formation in such a technique is to provide one labeled antibody and an unlabeled antibody bound to a solid phase support such that the complex can readily be isolated. In this example, the amount of labeled antibody associated with the solid phase is directly proportional to the amount of analyte in the test sample.

An alternative technique is the "competitive" assay. In one example of a competitive assay, the capture mechanism again may use an antibody attached to an insoluble solid phase, but a labeled analyte (rather than a labeled antibody) competes with the analyte present in the test sample for binding to the immobilized antibody. Similarly, an immobilized analyte can compete with the analyte of interest for a labeled antibody. In these competitive assays, the quantity of captured labeled reagent is inversely proportional to the amount of analyte present in the sample.

Despite their great utility, there are disadvantages with such assay methods. First, the heterogenous reaction mixture of liquid test sample and soluble and insoluble assay reagents, can retard the kinetics of the reaction. In comparison to a liquid phase reaction wherein all reagents are soluble, i.e. a homogeneous reaction mixture, the heterogenous reaction mixture can require longer incubation periods for equilibrium to be reached in the reaction mixture between the insoluble solid phase system, the free analyte in the test sample, the soluble labeled reagent, and the newly formed insoluble complex. Second, conventional methods of attaching binding members to the solid phase, such as adsorption of antibody to the solid phase, can produce a solid phase which will readily bind substances other than the analyte. This is referred to as nonspecific binding and can interfere with the detection of a positive result. Third, with conventional immobilization methods, separate batches of manufactured solid phase reagents can contain variable amounts of immobilized binding member.

With regard to the manufacture of solid phase devices for use in binding assays, there are a number of assay devices and procedures wherein the presence of an analyte is indicated by the analyte's binding to a labeled reagent and/or a complementary binding member that is immobilized on a solid phase such as a dipstick, test strip, flow-through pad, paper, fiber matrix or other solid phase material. Such a specific binding reaction results in a distribution of the labeled reagent between that which is immobilized upon the solid phase and that which remains free. Typically, the presence or amount of analyte in a test sample is indicated by the extent to which the labeled reagent becomes immobilized upon the solid phase.

The use of porous test strips in the performance of specific binding assays is also well-known. In a sandwich assay procedure, a test sample is applied to one portion of the test strip and is allowed to migrate through the strip material by means of capillary action. The analyte to be detected or measured passes through the test strip material, either as a component of the fluid test sample or with the aid of an eluting or chromatographic solvent which can be separately added to the strip. The analyte is thereby transported into a detection zone on the test strip wherein an analyte-specific binding member is immobilized. The extent to which the analyte becomes bound in the detection zone can be determined with the aid of a labeled analyte-specific binding member which may be incorporated in the test strip or which may be applied separately to the strip.

Examples of devices based upon these principles include those described the following patents and patent applications. Deutsch et al. describe a quantitative chromatographic test strip device in U.S. Pat. Nos. 4,094,647, 4,235,601 and 4,361,537. The device comprises a material capable of transporting a solution by capillary action. Different areas or zones in the strip contain the reagents needed to perform a binding assay and to produce a detectable signal as the analyte is transported to or through such zones. The device is suited for chemical assays as well as binding assays which are typified by the binding reaction between an antigen and a complementary antibody.

Many variations on the device of Deutsch et al. have been subsequently disclosed. For example, Tom et al. (U.S. Pat. No. 4,366,241) disclose a bibulous support with an immunosorbing zone, containing an immobilized specific binding member. The test sample is applied to the immunosorbing zone, and the assay result is read at the immunosorbing zone.

Weng et al. (U.S. Pat. Nos. 4,740,468 and 4,879,215) also describe a test strip device and methods for performing a binding assay. The device is used with a test solution containing the test sample, suspected of containing the analyte of interest, and a labeled specific binding member which binds to the analyte. The assays involve both an immobilized second binding member, which binds to the labeled binding member, and an immobilized analog of the analyte, which removes unbound labeled binding member from the assay system. Greenquist et al. (U.S. Pat. Nos.

4,806,311 and 4,806,312) describe a layered assay device for performing binding assays similar to those of Weng et al., wherein a first immobilized reagent such as an analyte-analog is used to remove unbound materials from the reaction mixture prior to the passage of the reaction mixture passage to a subsequent detection layer.

Rosenstein (European Patent Office Publication No. 0 284 232) and Campbell et al. (U.S. Pat. Nos. 4,703,017) describe assay methods and devices for performing specific binding assays, wherein the preferred detectable label is a colored particle consisting of a liposome containing a dye. Bahar, et al. (U.S. Pat. No. 4,868,108) describe an assay method and device for performing a specific binding assay, wherein the device involves a multizoned support through which test sample is transported and an enzyme/substrate detection means. Eisinger et al. (U.S. Pat. No. 4,943,522) describe an assay method and a device for performing specific binding assays, using a multizoned large-pored lateral flow membrane through which test sample is transported by capillary action.

Ullman et al. (European Patent Application No. 87309724.0; Publication No. 0 271 204) is related to the previously described Weng et al. patents (U.S. Pat. Nos. 4,740,468 and 4,879,215). Ullman et al. describe the preparation of a test solution containing an analyte-analog and a test sample suspected of containing the analyte. The test solution is contacted to a bibulous material having two sequential binding sites: the first binding site containing a specific binding pair member capable of binding the analyte and the analyte-analog, the second binding site capable of binding that analyte-analog which is not bound at the first binding site.

Cerny E. (International Application No. PCT/US85/02534; Publication No. WO 86/03839) describes a binding assay wherein a test solution, containing the test sample and a labeled test substance, is allowed to diffuse through a solid phase to provide a measurable diffusion pattern. The resultant diffusion pattern has a diameter which is greater than the diameter of the diffusion pattern of the labeled test substance alone.

Zuk et al. (U.S. Pat. No. 4,956,275) describe a method and device for detecting an analyte by means of a sensor apparatus. An analyte-related signal is measured at two or more sites on the assay device by means of the sensor apparatus, and the mathematical relationship between the measurements provides a value (e.g., difference, ratio, slope, etc.) which is compared against a standard containing a known amount of analyte.

Hochstrasser (U.S. Pat. No. 4,059,407) discloses a dipstick device which can be immersed in a biological fluid for a semi-quantitative measurement of the analyte in the fluid. The semi-quantitative measurement of the analyte is accomplished by using a series of reagent-containing pads, wherein each pad in the series will produce a detectable color (i.e., a positive result) in the presence of an increasing amount of analyte. Also of interest in the area of dipstick devices are U.S. Pat. Nos. 3,802,842, 3,915,639 and 4,689,309.

Grubb et al. (U.S. Pat. No. 4,168,146) describe the use of a porous test strip material to which an antigen-specific antibody is immobilized by covalent binding to the strip. The test strip is immersed in a solution suspected of containing an antigen, and capillary migration of the solution up the test strip is allowed to occur. As the antigen moves up the test strip it binds to the immobilized antigen-specific antibody. The presence of antigen is then determined by wetting the strip with a second antigen-specific antibody to which a fluorescent or enzyme label is covalently bound. Quantitative testing can be achieved by measuring the length of the strip that contains bound antigen. Variations on such a test strip are disclosed in U.S. Pat. No. 4,435,504 which employs a two enzyme indicator system; U.S. Pat. No. 4,594,327 which discloses the addition of a binding agent to whole blood samples which causes the red blood cells to aggregate at the area of the strip adjacent to the air/liquid interface; and U.S. Pat. No. 4,757,004 which discloses a means for controlling the shape of the fluid front migrating along the test strip. The assay principle is further described in Zuk et al., Enzyme Immunochromatography—A Quantitative Immunoassay Requiring No Instrumentation, Clinical Chemistry, 31(7): 1144–1150, 1985.

Further examples of strip-type diagnostic devices include the following. Swanson et al. (EP 088 636) describe an apparatus for the quantitative determination of an analyte involving a fluid-permeable solid medium containing a predetermined number of successive spaced reaction zones. The reaction zones include a reactant capable of reacting with the analyte to produce a detectable signal; the greater the number of zones producing a detectable signal, the greater the amount of analyte in the test sample. Freisen et al. (U.S. Pat. No. 4,861,711) describe a sheet-like diagnostic device containing several functional sectors through which the sample must pass. At least one of the sectors includes an immobilized reagent having a biological affinity for the analyte or an analyte complex.

Gordon et al. (U.S. Pat. No. 4,956,302) describe a test strip device characterized by having the analyte, test sample and/or eluting solvent migrate through the device in a single direction, thereby sequentially contacting reagent-containing zones or detection zones. Gordon et al. (U.S. Pat. No. 4,960,691) describe a device that includes one or more bounded pathways to direct the migration of the analyte, test sample and/or eluting solvent through the reagent-containing zones and detection zones in a predetermined order.

A variety of binding methods have been used to remove an analyte from a test solution. Bolz et al. (U.S. Pat. No. 4,020,151) describe a solid-phase assay for the quantitation of antigens or antibodies in a test sample. The sample antigen or antibody is adsorbed directly onto a solid support surface, such as anion exchange resin, and the support is then exposed to a labeled specific binding member that is immunologically reactive with the sample antigen or antibody.

Schick et al. (U.S. Pat. No. 4,145,406) describe the use of an ion exchange adsorbent to non-specifically bind protein. Marshall et al. (U.S. Pat. No. 4,211,763) describe a method for determining thyroid function involving an anion exchange resin to bind protein and form an agglomerate. Tabb et al. (U.S. Pat. No. 4,362,697) describe a test device involving the use of a copolymer of vinyl pyrrolidone as an enhancer substance. Giegel et al. (U.S. Pat. No. 4,517,288) describe a method for conducting a ligand assay requiring the adsorption or immunological binding of an analyte-specific binding member to a porous medium, followed by the application of the analyte to the porous medium.

Other assay methods involve the use of auxiliary specific binding members. Tanswell et al. (U.S. Pat. No. 4,624,930) describe a process for determining the presence of a polyvalent antigen by incubating the antigen with three receptors; a first and a third receptor which bind to the antigen and a second receptor, bound to a solid support, which specifically binds to the first receptor. Valkirs et al. (U.S. Pat. No.

4,727,019) describe a method and device for ligand-receptor assays, as in Tanswell et al., wherein an anti-receptor (e.g., avidin) is immobilized on a porous member and binds to a receptor (e.g., an analyte-specific antibody bound to biotin) which is bound to the target ligand. Wolters et al. (U.S. Patent Number 4,343,896) describe the use of ancillary specific binding members to prepare or complete detectable complexes, i.e., the use of a third antibody in a binding assay to complete a detectable analyte-binding member complex. W. Georghegan (U.S. Pat. No. 4,880,751) describes a method for preparing an immunoadsorption matrix by adsorbing the F(c) portion of a selected IgG molecule onto a charged surface. Parikh et al. (U.S. Pat. No. 4,298,685) describe the use of a conjugate of biotin and an anti-analyte antibody together with an inert support bearing immobilized avidin. The specific binding of the avidin and biotin components enables the immobilization of the antibody on the inert support.

Alternative separation methods include the use of a magnetic solid phase, polymerization techniques and the formation of analyte complexes having characteristics different than the non-complexed analyte. Ullman et al. (U.S. Pat. No. 4,935,147) describe a method for separating charged suspended non-magnetic particles from a liquid medium by contacting the particles with charged magnetic particles and a chemical reagent. The chemical reagent forms non-specific bonds between the magnetic and non-magnetic particles to produce a magnetic coaggregate. A magnetic field gradient is applied to the reaction container to concentrate the coaggregate to one part of the container, and the liquid medium is then decanted.

Longoria et al. (U.S. Pat. No. 4,948,726) describe an assay method involving the reaction of antigen and antibody molecules to form an antigen/antibody complex that uniquely exhibits an ionic charge that is different from the ionic charges of the individual molecules. A filter paper matrix is then chosen for its unique affinity for the antigen/antibody complex. Milburn et al. (U.S. Pat. No. 4,959,303) describe an assay wherein antigen from a test sample and an antibody specific for the antigen are incubated under conditions sufficient for the antibody to bind to the support when the antigen is bound to the antibody.

Vandekerckhove (U.S. Pat. No. 4,839,231) describes a two-stage, protein immobilization process involving an initial separation or isolation of target proteins in a gel, such as a polyacrylamide electrophoresis gel, followed by the transfer of those isolated proteins to the surface of a coated support for immobilization. The coated support is prepared by contacting a chemically inert support material (which material bears negatively charged groups) with a solution of either polyvinylpyridine or polymer (which polymer bears positively charged groups). The capacity of the positively charged polymer to form ionic linkages with the negatively charged groups of the support material results in the formation of an insoluble polymeric film on the support.

Monji et al. (U.S. Pat. No. 4,780,409) describe a reactant conjugated to a temperature-sensitive or salt-sensitive polymer which will precipitate from a test solution when the temperature or salt concentration of that solution is adjusted to an appropriate level. Marshall (U.S. Pat. No. 4,530,900) describes a reactant conjugated to a soluble polymer, wherein the polymer is rendered insoluble for removal from solution and is physically removed from the test solution by filtration or centrifugation. Marshall discloses two means by which this reactant-polymer conjugate is rendered insoluble: the lowering of the pH of the solution or the addition of a salt as in Monji et al. Marshall goes on to describe that the insolubilized conjugate is then precipitated, removed from the test solution and finally resolubilized to form a second solution prior to the detection of analyte.

As will be appreciated from the review of the background art, there is significant activity in the test strip field. There is a growing demand for devices that require few or no manipulative steps to perform the desired assay, for devices that can be used by relatively untrained personnel, and for devices that provide results which are minimally affected by variations in the manner in which the assay is performed. Further considerations are the ease with which the resultant detection signal may be observed as well as the ease with which any signal substance immobilized at the detection site can be distinguished from the signal substance which passed through the detection site. In addition, a device manufacturing format has long been sought which will enable the production of a "generic" device, i.e., an assay device for which the capacity of use is defined by the reagents used in the performance of the assay rather than the reagents used in the manufacture of the device.

SUMMARY OF THE INVENTION

The present invention provides novel binding assay methods for determining the presence or amount of an analyte in a test sample. The assay involves a capture reagent, containing a first binding member conjugated to a polymeric anion such as carboxymethylamylose, an indicator reagent containing a second binding member with a detectable label, and a solid phase material containing a reaction site made of a polymeric cation substance. The specific binding members of the capture reagent and indicator are chosen for the formation of a complex with the analyte in a sandwich assay, a competitive assay or an indirect assay, thereby forming a detectable complex in proportion to the presence or amount of the analyte in the test sample.

The solid phase is contacted with the capture reagent and the test sample, whereby the polymeric cation of the solid phase attracts and attaches to the polymeric anion of the capture reagent, thereby immobilizing the capture reagent and complexes thereof upon the solid phase. The solid phase may then be contacted with the indicator reagent, whereby the indicator reagent becomes bound to the immobilized capture reagent, or complex thereof, in proportion to the amount of analyte present in the test sample. Typically, the indicator reagent associated with the solid phase is then detected to determine the presence or amount of the analyte in the test sample. Alternatively, that indicator reagent which remains unbound can be detected.

The present invention also enables the production of a generic solid phase device for use in specific binding assays. Assay procedures for many different analytes can use the same solid phase material which contains a predetermined zone of anionic or cationic capture polymer rather than an immobilized binding member capable of binding only a specific analyte as found in conventional flow-through and test strip devices.

The specific binding member component of the capture reagent can be either a hapten or a macromolecule. The charged capture reagent enables homogeneous assay and separation reactions wherein the reaction complexes can be removed from the reaction mixture by contacting the mixture with an oppositely charged solid phase. Virtually any binding assay (sandwich assays, competitive assays, indirect assays, assays using ancillary specific binding members, inhibition assays, etc.) can be adapted to use the novel capture reagents and ion-capture techniques of the present invention.

The present invention provides two major advancements to the field of specific binding assays: a) the use of liquid phase kinetics facilitates the formation of a complex from the homogeneous mixture of analyte and assay reagent specific binding members, and b) the ion-capture technique increases the potential number of complexes that can be immobilized on a solid support. If the advantages of liquid phase kinetics are not sought, the present invention also provides an efficient method of immobilizing binding members on a solid phase through a method other than absorption, adsorption or covalent binding.

The novel capture reagent of the present invention can also be used in a separation procedure. A liquid sample containing an analyte to be separated from the sample is mixed with the capture reagent and reacted to form a charged analyte/capture reagent complex. Following the specific binding reaction, the solution is contacted to an oppositely charged solid phase which attracts, attaches to, and separates the newly formed complex from the liquid sample.

DETAILED DESCRIPTION OF THE INVENTION

The assay methods and reagents of the present invention can be used in a variety of immunoassay formats. The present invention, however, is not limited to immunoreactive assays. Any assays using specific binding reactions between the analyte and assay reagents can be performed.

Definitions

The following definitions are applicable to the present invention.

The term "specific binding member", as used herein, refers to a member of a specific binding pair, i.e., two different molecules where one of the molecules through chemical or physical means specifically binds to the second molecule. The complementary members of a specific binding pair may also be referred to as a ligand and a receptor. In addition to the well-known example of the antigen and antibody specific binding pair, alternative specific binding pairs are exemplified by the following: biotin and avidin, carbohydrates and lectins, complementary nucleotide sequences (including probe and capture nucleic acid sequences used in DNA hybridization assays to detect a target nucleic acid sequence), complementary peptide sequences (including those formed by recombinant methods), effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte (an analyte-analog) can be used so long as it has at least one epitope in common with the analyte. Immunoreactive specific binding members include antigens, haptens, antibodies, and complexes thereof including those formed by recombinant DNA methods or peptide synthesis. An antibody can be a monoclonal or polyclonal antibody, a chimetic antibody, a recombinant protein or a mixture(s) or fragment(s) thereof, as well as a mixture of an antibody and other specific binding members. The details of the preparation of such antibodies and their suitability for use as specific binding members are well-known to those skilled-in-the-art.

The term "hapten", as used herein, refers to a partial antigen or non-protein binding member which is capable of binding to an antibody, but which is not capable of eliciting antibody formation unless coupled to a carrier protein.

The term "test sample", as used herein, refers to virtually any liquid sample. The test sample can be derived from any desired source, such as a physiological fluid, for example, blood, saliva, ocular lens fluid, cerebral spinal fluid, sweat, urine, milk, ascites fluid, mucous, syncvial fluid, peritoneal fluid, amniotic fluid or the like. The liquid test sample can be pretreated prior to use, such as preparing plasma from blood, diluting viscous liquids, etc. Methods of pretreatment can also involve separation, filtration, distillation, concentration, inactivation of interfering components, and the addition of reagents. Besides physiological fluids, other liquid samples such as water, food products and the like can be used. In addition, a solid test sample can be used once it is modified to form a liquid medium.

The term "analyte", as used herein, refers to the substance to be detected in or separated from the test sample by means of the present invention. The analyte can be any substance for which there exists a naturally occurring specific binding member or for which a specific binding member can be prepared. In addition, the analyte may bind to more than one specific binding member. "Analyte" also includes any antigenic substances, haptens, antibodies, and combinations thereof. The analyte can include, but is not limited to, a protein, a peptide, an amino acid, a hormone, asteroid, a vitamin, a drug including those administered for therapeutic purposes as well as those administered for illicit purposes, a bacterium, a virus, and metabolites of or antibodies to any of the above substances.

The term "analyte-analog", as used herein, refers to a substance which cross-reacts with a binding member specific for the analyte, although the analyte-analog may react with the binding member to a greater or a lesser extent than does the analyte itself. The analyte-analog can include a modified analyte as well as a fragmented or synthetic portion of the analyte molecule so long as the analyte-analog has at least one epitopic site in common with the analyte of interest.

The term "label", as used herein, refers to any substance which directly or indirectly attaches to a specific binding member and which is capable of producing a signal that is detectable by visual or instrumental means. Various suitable labels for use in the present invention can include chromogens; catalysts; fluorescent compounds; chemiluminescent compounds; radioactive labels; direct visual labels including colloidal metallic and non-metallic particles, dye particles, enzymes or substrates, or organic polymer latex particles; liposomes or other vesicles containing signal producing substances; and the like.

A large number of enzymes suitable for use as labels are disclosed in U.S. Pat. No. 4,275,149, columns 19–23, the disclosure of which is hereby incorporated by reference. For example, an enzyme/substrate signal producing system useful in the present invention involves the enzyme alkaline phosphatase and the substrate nitro blue tetrazolium-5-bromo-4-chloro-3-indolyl phosphate or a derivative or analog thereof.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this system.

In an especially preferred embodiment of the present invention, a visually detectable, colored particle can be used as the label component of the indicator reagent, thereby providing for a direct colored readout of the presence or concentration of the analyte in the sample without the need for the addition of other signal producing reagents. Materials for use as the colored particles are colloidal metals, such as gold, and dye particles as disclosed in U.S. Pat. Nos. 4,313,734 and 4,373,932 the disclosures of which are hereby incorporated by reference. The preparation and use of non-metallic colloids, such as colloidal selenium particles, are disclosed in U.S. Pat. No. 4,954,452 the disclosure of which is hereby incorporated by reference. The use of colloidal particle labels in immunochromatography is disclosed in co-owned U.S. Pat. No. 5,120,643 which is hereby incorporated by reference. Organic polymer latex particles for use as labels are disclosed in co-owned and copending U.S. patent application Ser. No. 248,858, filed Sep. 23, 1988 the disclosure of which is hereby incorporated by reference.

The term "signal producing component", as used herein, refers to any substance capable of reacting with the analyte or another assay reagent to produce a reaction product or signal that indicates the presence or amount of the analyte and that is detectable by visual or instrumental means. "Signal production system", as used herein, refers to the group of assay reagents that are used to produce the desired reaction product or signal. For example, one or more signal producing components can be used to react with a label and generate the detectable signal. For example, when the label is an enzyme, amplification of the detectable signal is obtained by reacting the enzyme with one or more substrates or additional enzymes to produce a detectable reaction product.

The term "indicator reagent", as used herein, refers to a specific binding member which is attached or which becomes attached to a label. The indicator reagent produces a detectable signal at a level relative to the amount of an analyte in the test sample. Generally, the indicator reagent is detected or measured after it is captured on the solid phase material, but the unbound indicator reagent can also be measured to determine the result of an assay.

The specific binding member of the indicator reagent is capable of binding either to the analyte as in a sandwich assay, to the capture reagent as in a competitive assay, or to an ancillary specific binding member to complete a detectable complex. The label, as described above, enables the indicator reagent to produce a detectable signal that is related to the presence or amount of analyte in the test sample. The specific binding member component of the indicator reagent enables the indirect binding of the label to the analyte, to an ancillary specific binding member or to the capture reagent. The selection of a particular label is not critical, but the label will be capable of generating a detectable signal either by itself, such as a visually detectable signal generated by colored organic polymer latex particles, or in conjunction with one or more additional signal producing components, such as an enzyme/substrate signal producing system. A variety of different indicator reagents can be formed by varying either the label or the specific binding member; it will be appreciated by one skilled-in-the-art that the choice involves consideration of the analyte to be detected and the desired means of detection.

As mentioned above, the label can become attached to the specific binding member during the course of the assay. For example, a biotinylated anti-analyte antibody may be reacted with a labeled streptavidin molecule. Any suitable combination of binding members and labels can be used.

The term "capture reagent", as used herein, refers to an unlabeled specific binding member which is attached to a charged substance. The attachment of the components is essentially irreversible and can include covalent mechanisms. The specific binding member can be a small molecule, such as a hapten or small peptide, so long as the attachment to the charged substance does not interfere with the binding member's binding site. The binding member component of the capture reagent is specific either for the analyte as in a sandwich assay, for the indicator reagent or analyte as in a competitive assay, or for an ancillary specific binding member, which itself is specific for the analyte.

The charged substance component of the capture reagent can include anionic and cationic monomers or polymers. For example, anionic polymers include polyglutamic acid (PGA), anionic protein or derivatized protein such as albumin, anionic polysaccharides such as heparin or alginic acid, polyaspartic acid, polyacrylic acid, and polyamino acids having a net negative charge at a pH appropriate for the specific binding reaction (such as a pH in the range of 4 to 10.) Furthermore, the specific binding member can be joined to more than one charged monomer or polymer to increase the net charge associated with the capture reagent.

The novel capture reagents of the present invention are used to facilitate the observation of the detectable signal by substantially separating the analyte and/or the indicator reagent from other assay reagents and the remaining test sample components. In its most advantageous use, the capture reagent is reacted with the test sample and assay reagents in a homogeneous reaction mixture. Following the formation of the desired specific binding member complexes, the complexes involving a capture reagent are removed from the homogeneous reaction mixture by contacting the homogeneous reaction mixture to a solid phase that is oppositely charged with respect to the charge of the capture reagent.

In one embodiment of the present invention, a negatively charged capture reagent can be prepared by conjugating the selected specific binding member to one or more activated polymeric anionic molecules and conjugate bases thereof represented by the general formula:

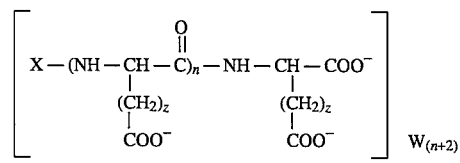

wherein n is about 10 to about 500; z is about 1 to about 6; W is chosen from $H^+$, $Na^+$, $K^+$, $Li^+$, amine salts such as $H^{+NR}_3$, and derivatives thereof; and X is virtually any reactive group or moiety having a reactive group that enables the chemical binding of the specific binding member and the polymer. "X" can be an amine-reactive group or moiety, a thiol-reactive group or moiety, or a thiol group or moiety represented by —A—SH wherein A is a spacer arm. For example, a specific binding member having an amino group can be conjugated to an activated PGA anionic molecule having an amine-reactive moiety. The amine-reactive moieties enable the binding of the activated polymer to an amino group on a specific binding member and include, but are not limited to, those represented by the following formulas:

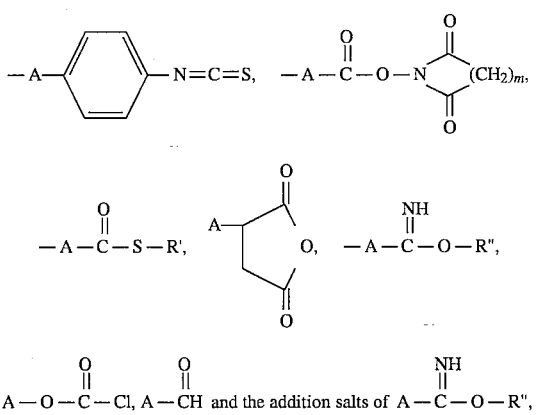

wherein m is two or three, R' is a sulfur stabilizer and R" is an aliphatic or aryl group. Sulfur stabilizers include, but are not limited to, 2-pyridyl, 4-pyridyl and 5-nitro-2-pyridyl groups. "A" represents a spacer of about one to about thirty atoms including, but not limited to, carbon, nitrogen, sulfur and oxygen atom chains and combinations thereof such as polyether, polymethylene and polyamide, as well as aromatic spacers such as phenylthiocarbamyl.

Alternatively, a specific binding member having a thiol group can be conjugated to an activated polymer having a thiol-reactive moiety. The thiol-reactive moieties include, but are not limited to, those represented by the following formulas:

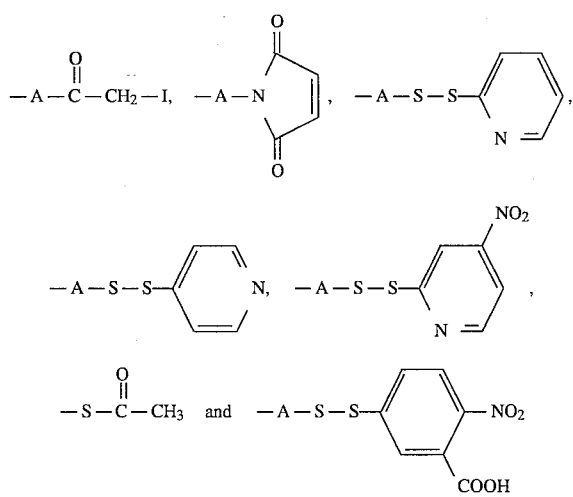

wherein A is a spacer of about one to about thirty atoms as described above. In yet another alternative, a specific binding member having a thiol-reactive group can be linked to an activated polymer having a thiol moiety such as —A—SH.

Typically, the negatively charged capture reagents of the following Examples were formed by reacting the desired specific binding member with an activated PGA molecule having modified terminal amino groups. Briefly, the modification method involved: 1) dissolving the PGA in a solvent (e.g., a water miscible aprotic solvent such as dioxane, dimethylformamide, 1-methyl-2-pyrrolidinone and dimethyl sulfoxide); 2) adding a proton absorbing reagent (e.g., 4-methyl morpholine) in the amount of about one equivalent per titratable carboxylic acid; 3) adding about a 2 to about a 100 molar excess of an amine-reactive modification reagent (e.g., 1,4-phenylene diisothiocyanate dissolved in dimethylformamide); 4) reacting the mixture; and 5) removing the unreacted amine-reactive modification reagent. Suitable proton absorbing reagents include alkali metal hydroxides such as sodium hydroxide, potassium hydroxide or lithium hydroxide, and tertiary amines such as 4-methyl morpholine and triethylamine.

The polymeric anionic molecule or the specific binding member will include one or more amino, carboxyl or thiol groups, or can be activated by the incorporation of an amino, carboxyl or thiol group, thereby enabling the chemical cross-linking of the specific binding member with the polymeric anionic molecule. "Activated species" refer to specific binding members and polymeric anionic molecules which contain a reactive group through the incorporation of a cross-linking or other activating agent. The amine-reactive modification reagents are a subclass of those reagents used to "activate" a specific binding member or polymeric anionic molecule, i.e., to prepare the specific binding member or the polymeric anionic molecule for chemical cross-linking. Activating agents also include thiol introducing agents such as the thiolanes (such as 2-iminothiolane), succinimidyl mercaptoacetates (such as N-succinimidyl-S-acetylmercaptoacetate), and disulfide compounds which are subsequently reduced to a thiol. The thiol introducing agents can be used to activate specific binding members and solid phase materials for their subsequent reaction with a thiol-reactive group.

Amine-reactive modification reagents include, but are not limited to, bifunctional crosslinking or coupling agents, such as succinic anhydride analogs, iminothiolane analogs, homobifunctional reagents and heterobifunctional reagents, which enable the chemical cross-linking of the specific binding member and the polymeric anionic molecule. Examples of homobifunctional reagents can be represented by the formula X—A—X wherein X is an amine-reactive group and A is a spacer of about one to about thirty atoms. Examples of heterobifunctional reagents can be represented by the formula X—A—Y, wherein X is an amine-reactive group, Y is a thiol-reactive moiety, a thiol moiety or a thiol precursor and A is a spacer of about one to about thirty atoms as described above. Proteinaceous specific binding members with cysteine residues at the protein's active site can have their activity decreased by the addition of a coupling agent, therefore the cysteine residues in the active site must be protected, by means known in the art, prior to reacting the protein with the coupling agent.

The term "coupling agent", as used herein, includes bifunctional crosslinking or coupling agents, i.e., molecules containing two reactive groups or "ends", which may be tethered by a spacer. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds, and NHS homobifunctional crosslinkers such as disuccinimidyl suberate (DSS) as well as the water soluble analogs, sulfo-NHS esters (Pierce 1989 Handbook and General Catalog; Pierce, Rockford, Ill.).

Other commercially available homobifunctional crosslinking reagents include, but are not limited to, the imidoesters such as dimethyl adipimidate dihydrochloride (DMA); dimethyl pimelimidate dihydrochloride (DMP); and dimethyl suberimidate dihydrochloride (DMS). The iminothiolane analogs can be represented by the general formula:

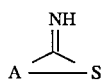

wherein A is a spacer of about 1 to about 5 atoms, e.g., 2-iminothiolane (Traut's Reagent.)

Commercially available heterobifunctional reagents suitable for use in the present invention include, but are not limited to, maleimido-NHS active esters coupling agents such as m-maleimidobenzoyl-N-hydroxy-succinimide ester (MBS); succinimidyl 4-(N-maleimidomethyl)cyclohexane-1-carboxylate (SMCC); succinimidyl 4-(p-maleimidophenyl)butyrate (SMPB) and derivatives thereof, including sulfosuccinimidyl derivatives such as sulfosuccinimidyl 4-(N-maleimido-methyl) cyclohexane-1-carboxylate (sulfo-SMCC); m-maleimidobenzoyl-sulfosuccinimide ester (sulfo-MBS) and sulfosuccinimidyl 4-(p-maleimidophenyl)butyrate (sulfo-SMPB) (Pierce). Other suitable heterobifunctional reagents include commercially available active halogen-NHS active esters coupling agents such as N-succinimidyl bromoacetate and N-succinimidyl(4-iodoacetyl)aminobenzoate (SIAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl -(2-pyridyldithio-)propionate (SPDP) (Pierce).

Yet another group of coupling agents includes the extended length heterobifunctional coupling agents described in co-owned and copending U.S. patent application Ser. Nos. 254,288 (filed Oct. 11, 1988) and 114,930 (filed Oct. 30, 1987) the disclosures of which are hereby incorporated by reference. The extended length heterobifunctional coupling agents include maleimido-NHS active ester reagents wherein the spacer is represented by the formula:

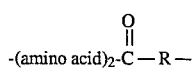

the amino acid is a substituted or unsubstituted amino acid, having from three to ten carbon atoms in a straight chain; n is from one to ten; and R is an alkyl, cycloalkyl, alkylcycloalkyl or an aromatic carboxylic ring. The term alkylcycloalkyl includes alkyl groups linked to cycloalkyl ring structures where the alkyl group links the cycloalkyl to a maleimide or carbonyl group. The term alkyl includes straight or branched alkyl groups, preferably lower alkyl groups having from one to six carbon atoms.

If a spacer is present, the spacer can be any molecular chain that is non-reactive, stable and non-binding to the analyte or other specific binding members with which it will be used. The length of the spacer can be varied and can range from the size of a single atom, to the sizes disclosed in U.S. Pat. Nos. 5,002,883 and 4,994,385 or larger.

The choice of the amine-reactive modification reagent, thiol introducing agent or other activating agent is not critical, but one skilled-in-the-art will know of suitable or preferred agents for use with the particular polymeric anionic molecule and specific binding member to be used in the diagnostic assay. Therefore, it will be appreciated by those skilled-in-the-art that the coupling agent or activating agent used in a given assay will generally be determined empirically.

Suitable thiol-reactive moieties of the heterobifunctional reagents include, but are not limited to, those represented by the following formulas:

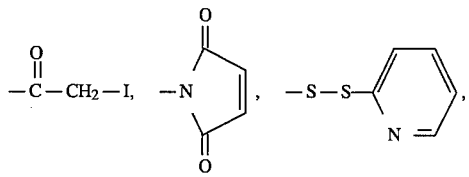

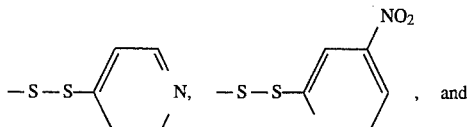

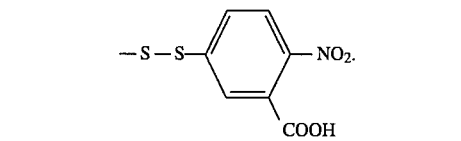

Suitable thiol precursor moieties include, but are not limited to, those represented by the following formulas:

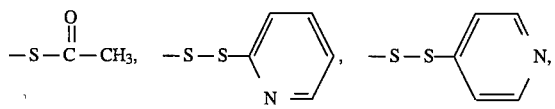

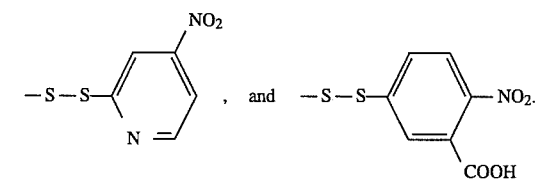

Suitable amine-reactive moieties include, but are not limited to, those represented by the following formulas:

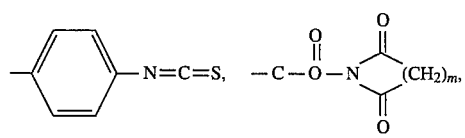

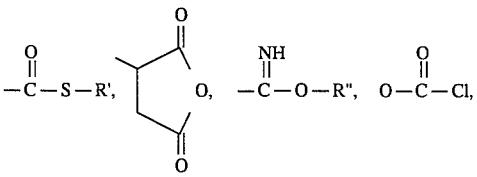

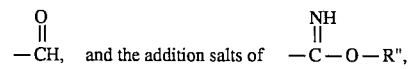

wherein m is 2 or 3, R' is a sulfur stabilizer, as described above, and R" is an aliphatic or aryl group.

In yet another embodiment of the present invention, a specific binding member having an amine-reactive group (e.g., an activated specific binding member) can be conjugated to a terminal amino group of the polymeric anionic molecule. Briefly, an example of a conjugation procedure involves: 1) dissolving PGA in a solvent (e.g., a water miscible aprotic solvent such as dioxane, dimethylformamide, 1-methyl-2-pyrrolidinone and dimethyl sulfoxide); 2) adding a proton absorbing reagent (e.g., an alkali metal hydroxide such as sodium hydroxide, potassium hydroxide, or lithium hydroxide, or a tertiary amine such as 4-methyl morpholine or triethylamine) in the amount of about one equivalent per titratable carboxylic acid; 3) adding about a 2 to about a 100 molar excess of amine-reactive specific binding member (e.g., phosgene-activated phenylcyclidine or phenylcyclidine-4-chloroformate); 4) reacting the mixture and 5) removing the unreacted amine-reactive specific binding member. Examples of suitable amine-reactive groups on specific binding members include, but are not limited to, the following:

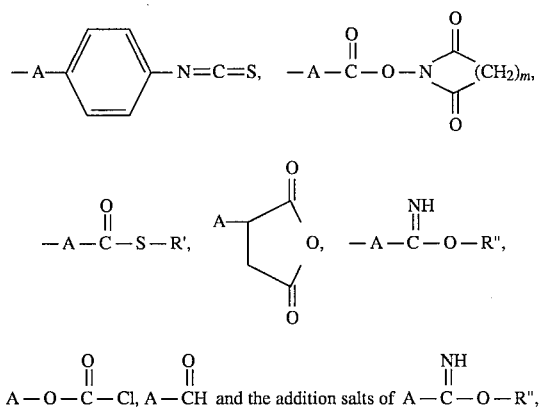

wherein A is a spacer of about one to about thirty atoms as described above, m is two or three, R' is a sulfur stabilizer and R" is an aliphatic or aryl group. An example of the preparation of a negatively charged capture reagent involves the reaction of a specific binding member (SBM) having an amino group and an activated PGA having an amine-reactive moiety. The resulting reaction and reaction product can be illustrated as follows:

In yet another embodiment of the present invention, a preferred anionic polymer for use in the capture reagent is carboxymethylamylose (CMA) due to its particular performance in various immunoassay configurations. The improved performance of capture reagents containing CMA can be attributed to the higher avidity of the CMA capture reagent for the cationic solid phase. This attribute is particularly advantageous in a two step sandwich assay format wherein a polyanion is used to block nonspecific binding of the indicator reagent to the cationic solid phase.

The term "ancillary specific binding member", as used herein, refers to any member of a specific binding pair which is used in the assay in addition to the specific binding members of the capture reagent and the indicator reagent. For example, in an assay an ancillary specific binding member may bind the analyte to a second specific binding member to which the analyte itself could not attach, or as in an inhibition assay the ancillary specific binding member may be a reference binding member. One or more ancillary specific binding members can be used in an assay.

The term "solid phase", as used herein, refers to any material which is insoluble, or can be made insoluble by a subsequent reaction. The solid phase can be chosen for its intrinsic charge and ability to attract the capture reagent, e.g., methylated wool, nylons, and special glasses having a positive charge. Alternatively, the solid phase can be pretreated with and retain a charged substance that is oppositely charged with respect to the charged substance of the capture reagent. For example, an anionic substance can be bound to a specific binding member to form the capture reagent, and a cationic substance can be applied to and retained by the solid phase, or vice versa.

Natural, synthetic, or naturally occurring materials that are synthetically modified, can be used as the cationic substance. A wide variety of proprietary polycations are available including tertiary and quaternary ammonium compounds and derivatives of ammonium compounds. Such polycationic materials include, but are not limited to, hexadimethrine bromide (Polybrene®; Sigma Chemical Company, St. Louis, Mo.), GAFQuat™ quaternary ammonium compounds (GAF Corporation, Wayne, N.J., 07470), diethylaminoethyl-dextran (Sigma), Merquat-100® compound (a cationic homopolymer of dimethyldiallylammonium chloride; Calgon Corporation, Pittsburgh, Pa.) and water soluble cellulose derivatives such as diallyldimethylammonium chloride-hydroxyethyl cellulose polymer (Celquat® L-200

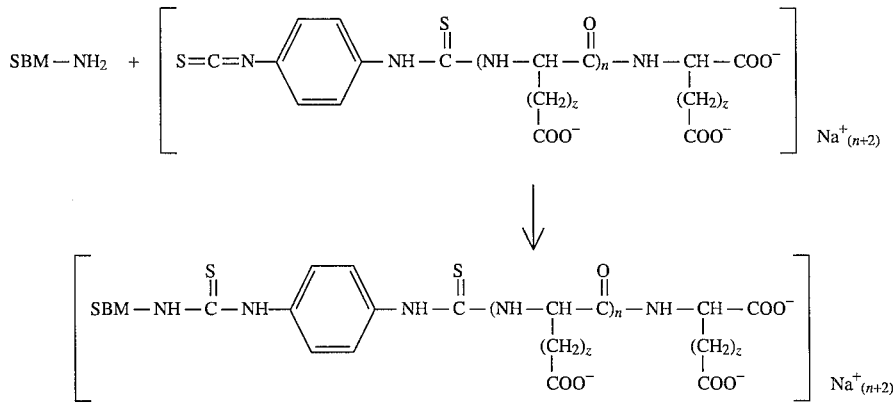

polymeric quaternary ammonium compounds and Celquat®

H-100 polymeric compounds, National Starch & Chemical Corporation, Bridgewater, N.J., 08807).

It was unexpectedly discovered that the cationic homopolymer of dimethyldiallylammonium chloride and other polycationic substances having a nitrogen content above about 2% (exclusive of counter ion) are particularly advantageous in preparing a solid phase that will undergo washing during the assay process. The use of such a polycationic substance to prepare a suitably charged solid phase resulted in a solid phase that could be subjected to a greater degree of manipulation without losing the capability to attract and retain the oppositely charged capture reagent. It was determined that polycationic substances having a nitrogen content above about 5% (exclusive of counter ion) were more preferred and that substances having a nitrogen content above about 10% (exclusive of counter ion) were most preferred.

An assay device based on the ion-capture technique can have many configurations, several of which are dependent upon the material chosen as the solid phase. In various device embodiments, the solid phase may involve polymeric or glass beads, microparticles, magnetic particles, tubes, sheets, plates, slides, wells, tapes, test tubes, layered films or the like, or any other material which has an intrinsic charge or which can retain a charged substance.

The novel ion-capture devices of the present invention involve a solid phase made of any suitable porous material. By "porous" is meant that the material is one through which the test sample can easily pass by capillary or wicking action and includes both bibulous and non-bibulous solid phase materials. For example, the solid phase can include a fiberglass, cellulose, or nylon pad for use in a flow-through assay device having one or more layers containing one or more of the assay reagents; a dipstick for a dip and read assay; a test strip for wicking or capillary action (e.g., paper, nitrocellulose, polyethylene) techniques; or other porous or open pore materials well-known to those skilled-in-the-art (e.g., polyethylene sheet material as manufactured by Porex Technologies Corporation, Fairburn, Ga., U.S.A.).

Natural, synthetic, or naturally occurring materials that are synthetically modified, can be used as a solid phase including polysaccharides, e.g., cellulose materials such as paper and cellulose derivatives such as cellulose acetate and nitrocellulose; silica; inorganic materials such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran, and gelatin; polymeric films such as polyacrylamide; and the like. The solid phase should have reasonable strength or strength can be provided by means of a support, and it should not interfere with the production of a detectable signal.

Preferred solid phase materials for flow-through assay devices include filter paper such as a porous fiberglass material or other fiber matrix materials as well as isotropically porous materials such as a polyethylene pad. The thickness of the material used will be a matter of choice, largely based upon the properties of the sample or analyte being assayed, e.g., the fluidity of the test sample.

To change or enhance the intrinsic charge of the solid phase, a charged substance can be applied directly to the solid phase material or to microparticles which are then retained by a solid phase support material. Alternatively, coated microparticles alone can be used as the charged solid phase by being retained in a column. By "retained" is meant that the particles on or in the solid phase support material are not capable of substantial movement to positions elsewhere within the support material. The particles can be selected by one skilled-in-the-art from any suitable type of particulate material and include those composed of polystyrene, polymethylacrylate, polypropylene, latex, polytetrafluoroethylene, polyacrylonitrile, polycarbonate, glass or similar materials. The size of the particles is not critical, although it is preferred that the average diameter of the particles be smaller than the average pore size of the support material being used.

Typically, the novel test strip and flow-through devices employing the ion-capture principles of the present invention are characterized by having the analyte, test sample and/or eluting solvent migrate through the device in a single direction, thereby sequentially contacting reagent-containing zones or detection zones. Alternatively, the novel devices of the present invention may be configured such that the analyte migrates radially from the sample application site to the reagent-containing zones or detection zones. In yet another embodiment, the novel devices may include one or more bounded pathways to direct the migration of the analyte, test sample and/or eluting solvent through the reagent-containing zones and detection zones in a predetermined order.

Uses for Ion-Capture Reagents

In accordance with the disclosure of the present invention, a sandwich assay can be performed wherein the capture reagent involves an analyte-specific binding member which has been bound to a charged substance such as an anionic polymer. The capture reagent is contacted with a test sample, suspected of containing the analyte, and an indicator reagent comprising a labeled analyte-specific binding member. The reagents can be mixed simultaneously or added sequentially, either singly or in combination to form a homogenous reaction mixture.

In the exemplary sandwich assay, a binding reaction results in the formation of a capture reagent/analyte/indicator reagent complex. The resultant complex is then removed from the excess assay reagents and test sample of the homogenous reaction mixture by means of a solid phase that is either inherently oppositely charged with respect to the capture reagent or that retains an oppositely charged substance, for example a cationic polymer. In the ion-capture assays, the oppositely charged solid phase attracts and attaches to the capture reagent/analyte/indicator reagent complex through the interaction of the anionic and cationic polymers. The complex retained on the solid phase is then detected by examining the solid phase for the indicator reagent. If analyte is present in the sample, then label will be present on the solid phase. The amount of label on the solid phase is proportional to the amount of analyte in the sample. The only major limitation inherent in the sandwich assay is the requirement for the analyte to have a sufficient size and appropriately orientated epitopes to permit the binding of at least two specific binding members. Other sandwich assays may involve one or more ancillary specific binding members to bind the analyte to the indicator reagent and/or capture reagent.

The present invention also can be used to conduct a competitive assay. In an exemplary competitive assay, the soluble capture reagent again includes a specific binding member which has been attached to a charged substance, such as an anionic polymer. The capture reagent is contacted, either sequentially or simultaneously, with the test sample and an indicator reagent that includes a second binding member which has been labeled with a signal generating compound. Either the capture reagent and analyte can compete in binding to the indicator reagent (e.g., the capture reagent and analyte are antigens competing for a labeled antibody), or the indicator reagent and analyte can compete in binding to the capture reagent (e.g., the indicator reagent is a labeled antigen which competes with the antigen analyte for binding to the antibody component of the capture reagent). A competitive binding or displacement reaction occurs in the homogeneous mixture and results in the formation of capture reagent/analyte complexes and capture reagent/indicator reagent complexes.

The resultant complexes are removed from the excess assay reagents and test sample by contacting the reaction mixture with the oppositely charged solid phase. The capture reagent complexes are retained on the solid phase through the interaction of the oppositely charged polymers. The complexes retained on the solid phase can be detected via the label of the indicator reagent. In the competitive assay, the amount of label that becomes associated with the solid phase is inversely proportional to the amount of analyte in the sample. Thus, a positive test sample will generate a negative signal. The competitive assay is advantageously used to determine the presence of small molecule analytes, such as small peptides or haptens, which have a single epitope with which to bind a specific binding partner. Other competitive assays may involve one or more ancillary specific binding members to bind the analyte to the indicator reagent and/or capture reagent.

For example, in an assay for theophylline, an anti-theophylline antibody (either monoclonal or polyclonal) can be conjugated with an anionic polymer to form a soluble capture reagent, and a competition for binding to that antibody can be established between labeled theophylline (i.e., indicator reagent) and the unlabeled theophylline of the test sample. After incubation, the homogeneous mixture can be contacted to a solid phase which retains a cationic polymer coating. The attraction between the oppositely charged ionic species of the capture reagent and the solid phase serves to separate the immunocomplex from the reaction mixture. The signal from the indicator reagent can then be detected. In this example, increased theophylline levels in the test sample will result in decreased signal generation associated with the solid phase.

In addition, the present invention can be used in an inhibition assay, such as the measurement of an antibody by inhibiting the detection of a reference antigen. For example, the capture reagent can include an antibody/anionic polymer conjugate and the indicator reagent can be a labeled antibody. The test sample, suspected of containing an antibody analyte, is mixed with a reference antigen with which the capture reagent and indicator reagent can form a detectable sandwich complex that can be immobilized upon the solid phase by the ion-capture reaction. The degree of inhibition of antigen uptake by the capture reagent is proportional to the amount of antibody analyte in the test sample, thus, as the concentration of the antibody analyte increases, the less reference antigen is available to complete the immobilized sandwich complex.

In general, once complex formation occurs between the analyte and the assay reagents, the oppositely charged solid phase is used as a separation mechanism: the homogeneous reaction mixture is contacted with the solid phase, and the newly formed binding complexes are retained on the solid phase through the interaction of the opposite charges of the solid phase and the capture reagent. If the user is not concerned with liquid phase kinetics, the capture reagent can be pre-immobilized on the solid phase to form a capture site.

The present invention can also be used for separating a substance from a liquid sample. For example, the capture reagent and solid phase can be used without an indicator reagent for the sole purpose of separating an analyte from a test sample. Furthermore, the capture reagent can be contacted with a soluble second charged substance which is oppositely charged with respect to the capture reagent. The second charged substance is not retained on the solid phase prior to contacting the sample to the solid phase material, but it attracts and attaches to the capture reagent such that the resultant assay complexes are retained on an oppositely charged solid phase.

When the complex of charged capture reagent and analyte (and/or indicator reagent) is contacted to the oppositely charged solid phase, the ionic attraction of the oppositely charged species governs the efficiency of the separation of the complex from the reaction mixture. The ionic attraction can be selected to provide a greater attraction than the immunological attraction of antibody for antigen, particularly when multiple polycationic and polyanionic species are included in the capture reagent and oppositely charged solid phase. A further advantage is that the "ion-capture" technique minimizes the nonspecific adsorption of interfering substances onto the solid phase, thereby offering improved accuracy of analysis. The ion-capture technique thereby enables the performance of an assay having a highly specific separation method, minimal nonspecific binding, and high sensitivity.

In one embodiment of the present invention, it was discovered that the addition of a nonspecific binding blocker reagent to the indicator reagent resulted in an increase in the signal to noise ratio. It was unexpectedly discovered that the nonspecific binding blocker could be a free polyanion even when the capture reagent used in the assay involved a polyanionic substance conjugated to a specific binding member. It would have been expected that the presence of a free or unbound polyanion would prevent, or at least reduce, the immobilization of the capture reagent on the solid phase. It was found, however, that the nonspecific blocker was more effective in inhibiting the direct, nonspecific binding of indicator reagent to the solid phase than it was in reducing the attachment of the polyanionic capture reagent to the polycationic solid phase. Suitable nonspecific binding blockers include, but are not limited to, dextran sulfate, heparin, carboxymethyl dextran, carboxymethyl cellulose, pentosan polysulfate, inositol hexasulfate and $\beta$-cyclodextrin sulfate.

It was also discovered that the amount of polyanionic nonspecific binding blocker added to the indicator reagent could be greater than the amount of polyanionic substance contained in the capture reagent. It was found that free polyanionic nonspecific binding blocker could be added to the indicator reagent in amounts 40,000 times the amount of polyanionic substance used in the capture reagent. Generally, the preferred amount of polyanionic blocker added to the indicator reagent is 50 to 14,000 times the amount of polyanionic substance used in the capture reagent. For two step sandwich assays, the preferred amount of polyanionic blocker added to the indicator reagent is 1000 to 2000 times that contained in the capture reagent.

An appropriate range of use can be determined for each analyte of interest. For example, in an assay to detect thyroid stimulating hormone (TSH) wherein dextran sulfate was added to the indicator reagent as a free polyanionic nonspecific binding blocker, suitable amounts of free polyanion ranged from 233 to 19,000 times that of the capture reagent, or about 0.1–8% dextran sulfate. As illustrated in the following Table, the preferred nonspecific binding blocker as well as the preferred amount of nonspecific binding blocker can be optimized for each analyte of interest.

| Analyte | Nonspecific Binding Blocker in the Indicator Reagent | |
|---|---|---|
| | Preferred | More Preferred |
| | % Dextran sulfate (MW 5,000) (blocker/capture reagent, w/w) | |
| TSH | 0.1–8 (233–19,000) | 0.5–2 (1,000–4,000) |
| T3 | 0.1–2 (2,000–40,000) | 0.1–0.2 (2,000–4,000) |
| | % Carboxymethyl cellulose (MW 250,000) (blocker/ capture reagent, w/w) | |
| hCG | 0.01–0.25 (0.44–11) | 0.025 (1.1) |
| HIV | 0–0.2 (0–20,000) | 0.05 (5,000) |

Moreover, it was discovered that the polyanionic nonspecific binding blocker could be added to the assay as a separate reagent, or it could be included as free polyanion in the capture reagent, in an ancillary binding member reagent, in a buffer reagent or in some other reagent used in the assay. For example, when free polyanion is included in the capture reagent, it can enhance the signal to noise ratio by neutralizing interfering materials which are contained either in the test sample itself or in the other assay reagents, or those which were introduced during the device manufacturing process. The following Table illustrates some preferred amounts of nonspecific binding blocker for different analytes of interest, wherein the free polyanion is contained in the capture reagent itself.

| Analyte | Nonspecific Binding Blocker in the Capture Reagent | |
|---|---|---|
| | Preferred | More Preferred |
| | % Dextran sulfate (MW 5,000) (blocker/capture reagent, w/w) | |
| Digoxin | 0–0.004 (0–222) | 0.004 (222) |
| T3 | 0.004–0.01 (66–165) | 0.004 (66) |

Depending upon the analyte of interest and the desired assay configuration, the preferred nonspecific binding blocker, as well as the optimization of its concentration and whether it is included as a component of another assay reagent, is selected by empirical techniques which can be performed without undue experimentation by one of ordinary skill in the art of binding assays. In only one known instance, i.e., the use of 0.005% dextran sulfate in the capture reagent of a competitive digoxin assay, was there an inhibition of the binding between the capture reagent and solid phase due to the addition of the nonspecific binding blocker.

Ion-Capture Assay Devices

As described above, ion-capture assay devices may include impermeable solid phase materials such as glass slides, magnetic particles, test tubes and plastic wells. However, it has also been discovered that the entire ion-capture assay can be performed in a porous solid phase material. The ion-capture assay devices of the present invention specifically involve any suitably absorbent, adsorbent, imbibing, bibulous, non-bibulous, isotropic or capillary possessing material (i.e., porous materials) through which a solution or fluid containing the analyte can pass. The solution can be pulled or pushed through the porous material by suction, hydraulic, pneumatic, hygroscopic, gravitational or capillary forces, or by a combination thereof.

Possible assay devices include, but are not limited to, a conventional chromatographic column, an elongated strip of porous material wherein the fluid flow is substantially linear, a sheet wherein the fluid flow is linear or radial, a pad of porous material or a device involving multiple layered sheets or pads. The novel devices of the present invention involve the production of test strips as well as flow through devices. For purposes of brevity, however, the following descriptions will focus on test strip devices, although the description of device zone can be applied to both strip-type or layered flow through-type devices. Those skilled-in-the-art will readily appreciate the applicability of the present invention to flow through device formats.

One advantageously used solid phase porous material for the production of a test strip is nitrocellulose. Especially when a membranous solid phase material is used, the test sample and indicator reagent may be mixed prior to initiating fluid flow through the solid phase to obtain a controlled, reproducible binding reaction between the analyte and the indicator reagent. Alternatively, the test device can further include a premixing application pad which is in fluid flow contact with the elongated strip and which optionally contains the indicator reagent. The material of the application pad should be chosen for its ability to premix the test sample with the indicator reagent. For example, if nitrocellulose is used as the solid phase, then a hydrophilic polyethylene material or glass fiber filter paper are suitable application pad materials. Alternatively, if a solid phase material such as glass fiber filter paper is used, then the indicator reagent can be reversibly immobilized on the elongated strip itself, either at the sample application site or at another site downstream from the application site. In yet other alternative devices and methods, the indicator reagent can be added to the device as a separate reagent solution, either sequentially or simultaneously with the test sample and/or capture reagent.

In alternative embodiments, a test strip or flow-through device may be made of a continuous piece of porous material containing diffusive or immobilized reagents to form the various reagent and detection zones. In yet another embodiment, a test strip can be made from more than one solid phase material such that the different materials are in fluid flow contact to allow the analyte to migrate from one material to another. The different materials may contain different diffusive or immobilized assay reagents, with the individual material being assembled into an elongated strip or flow through pad device. In yet a further embodiment, two or more zones of the device may overlap. For example, the sample application zone may also contain a diffusive assay reagent (e.g., indicator reagent, capture reagent, etc.) which reacts with the analyte to form a complex or reactive product which continues to migrate to other zones in or on the device. In a further example, the sample application zone may contain an immobilized assay reagent (e.g., polymer oppositely charged with respect to the capture reagent) which immobilizes the capture reagent or capture reagent complexes for detection. Again, those skilled-in-the-art will readily appreciate the applicability of the present invention to a variety of device formats wherein the indicator reagent is immobilized by directly or indirectly binding to a capture reagent conjugate that is in turn immobilized by an oppositely charged solid phase material.

a. Application Pad

If an application pad is used in a test strip device, it is placed in fluid flow contact with one end of the porous material, referred to as the proximal end, such that the test sample or an eluting solvent can pass or migrate from the application pad to the porous material. Fluid flow contact can include physical contact of the application pad to the porous material as well as the separation of the pad from the porous material by an intervening space or additional material which still allows fluid flow between the pad and the strip. Substantially all of the application pad may overlap the porous material to enable the test sample to pass through substantially any part of the application pad to the proximal end of the elongated strip. Alternatively, only a portion of the application pad might overlap the elongated strip material. The application pad can be any material which can transfer the test sample and/or eluting solvent to the elongated strip and which can absorb a volume of test sample and/or eluting solvent that is equal to or greater than the total volume capacity of the elongated strip.

Materials preferred for use in the application pad include nitrocellulose, porous polyethylene pads and glass fiber filter paper. The material must also be chosen for its compatibility with the analyte and assay reagents, for example, glass fiber filter paper was found to be the preferred application pad material for use in a human chorionic gonadotropin (hCG) assay device.

In addition, the application pad may contain one or more assay reagents either diffusively or non-diffusively attached thereto. Reagents which can be contained in the application pad include, but are not limited to, indicator reagents, ancillary specific binding members, test sample pretreatment reagents and signal producing system components. For example, in a preferred embodiment of an ion-capture device an indicator reagent is predeposited in the application pad during manufacture; this eliminates the need to combine test sample and indicator reagent prior to using the device. The isolation of assay reagents in the application pad also keeps interactive reagents separate and facilitates the manufacturing process. For example, the indicator reagent may be retained in the application pad in a dry state, and upon contact with the test sample or eluting solvent the indicator reagent is reconstituted and dispersed, thereby allowing its migration through the device. In yet another embodiment, the diffusive indicator reagent is situated on the test strip material itself at a position between the application pad and a detection zone on the test strip. In another embodiment, the diffusive indicator reagent is situated on the porous test strip material at a detection zone, and that indicator reagent which does not become immobilized at the detection zone due to the assay reaction will pass from the detection zone.

In a preferred ion-capture device, the application pad receives the test sample, and the wetting of the application pad by the test sample will perform at least two functions. First, it will dissolve or reconstitute a predetermined amount of reagent contained by the pad. Secondly, it will initiate the transfer of both the test sample and the freshly dissolved reagent to the porous material. The application pad may serve a third function as both an initial mixing site and a reaction site for the test sample and assay reagent.

In another preferred embodiment, the application pad contains both the indicator reagent and the capture reagent in a dried form. The addition of the test sample reconstitutes the assay reagents, thereby enabling their reaction with the analyte and the formation of a charged indicator reagent/analyte/capture reagent complex. The complex then migrates from the application pad to the porous test strip material for subsequent reaction with a polymeric material immobilized in a detection zone, wherein that polymeric material is oppositely charged with respect to the capture reagent. Alternatively, either the indicator reagent or the capture reagent may be contained in the porous test strip material between the application pad and the detection zone. Preferably, the capture reagent complex is allowed to form prior to or concurrent with the migration of the capture reagent into the detection zone.

In another embodiment of the present invention, gelatin is used to encompass all or part of the application pad. Typically, such encapsulation is produced by overcoating the application pad with gelatin. The effect of this overcoating is to increase the stability of the reagent contained by the application pad. The addition of test sample to the overcoated application pad causes the gelatin to dissolve, thereby rehydrating the predeposited assay reagent. In an alternative embodiment of the present invention, the reagent containing application pad is dried or lyophilized to increase the shelf-life of the device. Lyophilized application pads were found to produce stronger signals than air dried application pads, and the lyophilized application pads maintained stability for longer periods.

In another preferred embodiment, the assay devices of the present invention can be further modified by the addition of a filtration means. The filtration means can be a separate material placed above the application pad or between the application pad and the porous material. Alternatively, the application pad material can be chosen for its filtration capabilities. The filtration means can include any filter or trapping device used to remove particles or cells above a certain size from the test sample. For example, the filter means can be used to remove red blood cells from a sample of whole blood, such that plasma is transferred to the porous material. Such filter means are disclosed by U.S. Pat. No. 4,477,575 which is hereby incorporated by reference. Optionally, the filter means can include a reagent or reagents to remove particles or interferents from the test sample.

Another modification of the present invention involves the use of one or more additional layers of porous material placed between the application pad and the porous material or overlayed upon the application pad. Such an additional pad or layer can serve as a means to control the rate of flow of the test sample to or from the application pad. Such flow regulation is preferred when an extended incubation period is desired for the reaction of the test sample and the reagent(s) in the application pad. Alternatively, such a layer can contain an additional assay reagent(s) which is preferably isolated from the application pad reagents until the test sample is added. The flow control layer may also serve to prevent unreacted assay reagents from passing to the porous material.

b. Porous Test Strip Material

The porous material used in the novel ion-capture devices of the present invention may be any suitably absorbant, porous or capillary possessing material through which a solution containing the analyte can be transported by a wicking action. One preferred porous material for test strip devices is nitrocellulose. When nitrocellulose is used, however, the material of the optional application pad should be chosen for its ability to premix the test sample and one or more assay reagents: fluid flow through a nitrocellulose membrane is laminar and does not provide the more turbulent flow characteristics which allow the initial mixing of test sample and application pad reagents within the porous material. If nitrocellulose is used as the porous material, then Porex® hydrophilic polyethylene material or glass fiber filter paper are appropriately used as application pads to enable the mixing and reaction of the test sample and assay reagents within the application pad. An especially preferred porous material is glass fiber filter paper.

The particular dimensions of the porous strip material will be a matter of convenience, depending upon the size of the test sample involved, the assay protocol, the means for detecting and measuring the signal, and the like. For example, the dimensions may be chosen to regulate the rate of fluid migration, as well as the amount of test sample to be imbibed by the porous material and transported to or through the detection site.

As discussed above, in a binding assay the detection site is typically formed by directly or indirectly attaching a charged polymer to the porous material at a predetermined location. Direct attachment methods include adsorption, absorption and covalent binding. Indirect attachment methods include the use of insoluble microparticles, to which the charged reagent has been attached, wherein the particles are retained and immobilized in or on the porous support material. The means of attaching a reagent to the microparticles encompasses both covalent and non-covalent means, that is adhered, absorbed or adsorbed. It is preferred that ion-capture reagents be attached to the microparticles by covalent means.

It is also within the scope of this invention to attach more than one reagent to the microparticles which are then immobilized within the porous material. For example, to slow or prevent the diffusion of the detectable reaction product in an enzyme/substrate signal producing system, the substrate can be immobilized within the porous material. The substrate can be immobilized by direct attachment to the porous material by methods well-known in the art or the substrate may be immobilized by being covalently bound to insoluble microparticles which have been deposited in and/ or on the porous material.

The size of the particles may vary depending upon the type of porous material used as well as the type of material from which the particle is made. For example, in a glass fiber porous material, glass and polystyrene particles should be of sufficient size to become entrapped or immobilized in the pores of the porous material and not move when confronted by the migrating fluid. In the same glass fiber matrix, much smaller latex particles can be used because the latex particles unexpectedly affix themselves to the glass fibers by an unknown mechanism. Thus, unlike pore size dependent glass and plastic particles, the latex particles are pore size independent, and lot-to-lot variations in pore size of the porous material will not adversely affect the performance of the device. As a result, one particularly preferred binding assay device uses latex particles, having capture reagent attached thereto, distributed in a glass fiber porous material. The distribution of the microparticles or other reagents onto or into the matrix of the porous material can be accomplished by reagent printing techniques as are well-known to those skilled-in-the-art.

The ion-capture reagent, signal producing component or reagent-coated microparticles can be deposited singly or in various combinations on or in the porous material. They can be deposited in a variety of configurations to produce detection or measurement sites of varying shape. For example, a reagent can be deposited as a discrete situs having an area substantially smaller than that of the entire porous strip material.

Alternatively, the reagent can be distributed over the entire porous material in a substantially uniform manner to form a capture site or detection site that substantially includes the entire porous material. In this instance, the extent of signal production along the length of the detection site, or the distance of the detectable signal from the proximal end of the porous material, is then related to the amount of analyte in the test sample. The amount of analyte can be determined by the comparison of the length or distance of the resulting signal to those observed for calibrated standards.

In another embodiment, the reagent can be distributed as a narrow stripe. Use of the narrow stripe, rather than a uniform distribution of reagent, can serve to sharpen the image of the detectable signal on the porous material. Furthermore, more than one narrow parallel stripe can be distributed along the length of the porous material, wherein the reagent within each stripe is directed to a different analyte, thereby forming a multi-analyte assay device. As an addition to those devices in which the length or distance of analyte travel is measured, a scale of appropriate symbols, numbers or letters can be imprinted upon the porous material to aid in the measurement and thus the quantitation of analyte.

In another embodiment, the reagent can be distributed more lightly at one end of the porous material than at the other. In a competitive binding assay, this deposition of capture reagent in a gradient fashion provides for greater sensitivity at the end of the porous I 5 material having the lighter distribution, because of the more rapid displacement of the indicator reagent from the capture reagent binding sites by the analyte.

In alternative embodiments, the appropriate capture and signal producing reagents can be distributed in any pattern convenient for detection including, but not limited to, numerals, letters, dots and symbols such as "+/−", "%" or the like which display the detectable signal upon completion of the assay. Reaction matrices can optionally be prepared with the assay reagents incorporated into the material in an overlapping design, such that the reaction of one reagent completes one portion of a detectable pattern and a second reaction completes another portion of the detectable pattern. For example, one reaction may complete the vertical portion of a "cross" shaped design while a second reaction completes the horizontal portion of the cross. Alternatively, one portion of the design may be visible or detectable prior to performance of the assay, with a single reaction completing the overall design. The completion of the vertical portion alone would typically indicate a negative assay result, whereas completion of both portions of the detectable design would indicate a positive assay result. Any pattern or design may be used, however, wherein the partial formation of the design indicates other than a positive assay result and the complete formation of the design indicates a positive assay result. Such methods and devices are described in U.S. Pat. No. 4,916,056 the disclosure of which is hereby incorporated by reference.

In yet another embodiment, the reagents can be distributed as a series of parallel bars which traverse the width of the porous strip material and which are spaced from about the proximal end of the porous material to about the distal end, thereby creating a ladder-like capture situs configuration. As with the narrow-stripe configuration, the bars and the intervening spaces serve to sharpen the image of the signal produced on the porous material. The number of bars at which signal is detectable can be counted and correlated to the amount of analyte in the test sample. When the bars are spaced closely together, the device provides less analytical sensitivity but greater amounts of analyte can be measured. Alternatively, by spacing the bars further apart, increasingly greater sensitivity can be obtained. It is also within the scope of this invention to vary the sensitivity within different portions of the porous material depending upon whether greater discrimination sensitivity for the analyte is required at the high end or low end of its concentration range. Another variation of the parallel bar configuration involves the use of multiple capture or reaction reagents wherein the reagents within the capture and detection sites are directed to a different analyte, thereby forming a multi-analyte assay device.

The particular dimensions of the solid phase will be a matter of convenience and will depend upon the size of the test sample involved, the assay protocol and the means for detecting and measuring the signal. For example, the dimensions may be chosen to regulate the rate of fluid migration as well as the amount of test sample to be imbibed by the solid phase.

Predetermined amounts of assay reagents can be incorporated within the device, thereby reducing or avoiding the need for additional manipulation by the user. Thus, it is within the scope of this invention to incorporate more than one reagent within the device. For example, to slow or prevent the diffusion of the detectable reaction product in an enzyme/substrate signal producing system, the substrate can be immobilized within the test strip. The substrate can be immobilized on or in the test strip by methods well-known in the art, or the substrate may be immobilized by being covalently bound to insoluble microparticles which have been deposited in and/or on the test strip. More than one assay reagent may be present in any given reagent zone or site on the device so long as the reagents do not react until contacted with the test sample or eluting solvent.

The various signal display formats or patterns described above can also incorporate assay controls to confirm the efficacy of the assay reagents, the completion of the assay or the proper performance of the assay. Such controls are well-known to those skilled-in-the-art. It is also within the scope of this invention to have a reagent, at the distal end of the test strip device, which indicates the completion of the assay (i.e., an end of assay indicator to signal that the test sample has completed its migration through the device). For example, the completion of the assay may be shown by a change of color at the control site upon contact with the test solution, wicking solution or a signal producing component. Reagents which would change color upon contact with an aqueous test solution include the dehydrated transition metal salts, such as $CuSO_4$, $Co(NO_3)_2$, and the like. The pH indicator dyes can also be selected to respond to the pH of the buffered wicking solution. For example, phenolphthalein changes from clear to intense pink upon contact with a wicking solution having a pH range between 8.0–10.0.

A test sample can be contacted to the test strip by applying the test sample to an application site or by immersing the application site in the test sample. In a sheet-like device having radial capture and conjugate recovery sites, the sample is applied to a central application site. Prior to contacting the sample to the solid phase, the sample can also be mixed with additional reagents such as the indicator reagent, capture reagent, buffers or wicking reagents (i.e., reagents which facilitate the transport of the test sample through the solid phase). In a further embodiment, the test sample can be applied to one portion of the test strip, upstream of the capture site, with one or more of the additional reagents being applied to yet another portion of the test strip upstream of the test sample application site.

In yet another embodiment, the device can include an additional absorbent material positioned downstream from or beneath the capture site. It will be appreciated that the absorbent material can serve to increase the amount of test sample and indicator reagent which passes through the capture and detection sites on the solid phase.

When small quantities of non-aqueous or viscous test samples are applied to the device, it may be necessary to employ a wicking solution, preferably a buffered wicking solution, to facilitate the migration of the assay reagent(s) and test sample through the device. When an aqueous test sample is used, a wicking solution generally is not necessary but may be used to improve flow characteristics or adjust the pH of the test sample. In immunoassays, the wicking solution typically has a pH range from about 5.5 to about 10.5, and more preferably from about 6.5 to about 9.5. The pH is selected to maintain a significant level of binding affinity between the specific binding members and the analyte. When the label component of the indicator reagent is an enzyme, however, the pH must also be selected to maintain significant enzyme activity for color development in enzymatic signal production systems. Suitable buffers include, but are not limited to, phosphate, carbonate, barbital, diethylamine, tris(hydroxymethyl)-aminomethane (Tris), 2-amino-2-methyl-1-propanol and the like. The wicking solution and the test sample can be combined prior to contacting the test device, or they can be contacted to the application pad separately.

c. Flow-Through Assay Devices

Conventional flow-through devices have at least a substantially planar layer including a sample-contacting surface wherein a nondiffusive specific binding member is disposed for the immobilization of the analyte of interest. The layer is positioned such that when the device is used in the performance of a binding assay, at least a portion of the test sample that contacts the first surface passes through the first surface to an opposing second surface.

Typically, the flow-through devices include a second layer or absorbent means for absorbing fluid passing through first layer, wherein the absorbent means is in direct contact with the second surface of the first layer, or is in close enough proximity that fluid passing through the second surface is transported to the absorbent means. In modified devices, the absorbent means may be spaced from the first layer and can be contacted to the second surface of the first layer by subsequently pressing the layers together.

Optionally, the flow-through devices may also involve a filtering means disposed in relation to the first layer such that when the device is in use the test sample will pass through the filtering means prior to contacting the first surface. Furthermore, flow-control means may be disposed between the first layer and the absorbent means to adjust the rate of flow of fluids from the first layer. Back-flow control means may also be disposed between the first layer and the absorbent means to prevent the migration of signal producing substances from the absorbent means to the first layer.

The flow-through devices may also include an assay reagent layer or layers disposed in relation to the first layer, such that when the device is in use, sample fluid passes through the assay reagent layer prior to contacting the first surface. The assay reagent is typically resolubilized by the addition of test sample to the reagent layer and the reagent is then available for further reaction with the analyte or other reagents housed within the assay device. Other embodiments may include a filter layer or a combination filter/reagent layer. Still other devices may involve a removable filter and/or reagent layer.

The novel flow-through assay devices of the present invention, involve a contact surface wherein a charged polymer is disposed for the nonspecific binding and immobilization of the oppositely charged capture reagent and complexes thereof. The device may consist of a layer or a first layer in combination with one or more other device layers described above. For example, one or more pre-reaction layers may contain the indicator reagent and or the capture reagent such that the analyte is allowed to contact the assay reagents prior to contacting the ion-capture surface of the flow-through device.

In either the flow-through or test strip assay devices, one or more assay reagents, such as the indicator reagent or capture reagent, may be applied to the device during the performance of the assay. The preferred embodiments of the present invention, however, involve the incorporation of all necessary assay reagents into the assay device so that only a test sample, and in some instances a wicking solution or eluting solvent, need be applied to the device.

The present invention further provides kits for carrying out binding assays. For example, a kit according to the present invention can comprise the assay device with its incorporated reagents, and can optionally include a wicking solution and/or test sample pretreatment reagent as described above which are not incorporated in or on the device. Other assay components known to those skilled-in-the-art, such as buffers, stabilizers, detergents, non-specific binding inhibitors, bacteria inhibiting agents and the like can also be present in the assay device and wicking solution.

EXAMPLES

The following Examples illustrate preferred ways of making the novel materials of the present invention and performing assay procedures using those materials. The Examples, however, are intended only to be illustrative, and are not to be construed as placing limitations upon the scope of the invention, which scope is defined solely by the claims.

Example 1

Sandwich Assay for Carcinoembryonic Antigen (CEA)

a. Preparation of an Anti-CEA Antibody-PGA Capture Reagent

The following sequence of steps describes the chemistry employed for the preparation of an antibody/polyglutamic acid (PGA) conjugate, i.e., an antibody/anionic polymer capture reagent.

Preparation of a traceable anionic polymer: The sodium salt of PGA (one gram; $7.14 \times 10^{-5}$ mole; average molecular weight [MW] 14,000; Sigma) was converted to 3-(2 -pyridyl-dithio) propionyl-PGA (PDP-PGA) by the method of Tsukada, et al. (JNCI; 73; 721–729, 1984) with the following procedural modifications. The PDP-PGA was not reduced to the free sulfhydryl prior to the thiopropyl sepharose 6B isolation. Instead, the PDP-PGA was dissolved in 0.1M Na phosphate and 1 mM EDTA (pH 6.5) and stirred with thiopropyl sepharose 6B (60 ml; 30 grams; Pharmacia Chemicals, Uppsala, Sweden). After dialysis and lyophilization, a 24% yield of the PDP-PGA conjugate was obtained (0.244 grams; $1.72 \times 10^{-5}$ mole).

To ensure that the disulfide was maintained during the ensuing chemistries, the thiopyridyl group was exchanged for a 5-thio-2-nitrobenzoate (TNB) protecting group. A 100 mole excess of 1,4-dithreitol (MW 154.2) was added to a solution of the PDP-PGA (20 mg; $1.42 \times 10^{-6}$ mole) dissolved in 0.1M sodium phosphate (4.0 ml; pH 7), and the reaction was run for one hour at 40° C. The mixture was diluted to ten milliliters with 5.0 mM sodium acetate, 0.14M NaCl, and 1.0 mM EDTA (pH 5.5) and dialyzed in 2000 molecular weight cut off (MWCO) tubing against the dilution buffer. Dialysis was continued against distilled water, followed by lyophilization. The yield of thiopropyl-PGA (HS-PGA) was 13.5 mg. The HS-PGA (13.5 mg) was dissolved in 0.1M sodium phosphate (pH 7.0; $9.6 \times 10^{-7}$ mole) and reacted with a 10 mole excess of 5,5' dithiobis (2-nitrobenzoic acid) (DTNB) for one hour at room temperature. This mixture was diluted to ten milliliters with 0.1M sodium phosphate (pH 7) and dialyzed in 2000 MWCO tubing against the dilution buffer. Dialysis was continued against distilled water and was followed by lyophilization to produce 5-(2-nitrobenzoic dithio) propionyl-PGA (TNB-PGA; 8.5 mg; $6.07 \times 10^{-7}$ mole).

To trace the number of anionic polymer molecules attached to each capture reagent antibody, the TNB-protected PGA was then labeled with an ethylenediamine derivative of fluorescein. The TNB-PGA was loaded with an ethylenediamine derivatized fluorescein (EDA-Fl; MW 532) by dissolving TNB-PGA (8.5 mg) in dry N-N dimethylformamide (2.0 ml), treating with a 90 mole excess of N-methylmorpholine (MW 101.15), lowering the temperature to 0° C., and adding a 90 mole excess of isobutylchloroformate (MW 136.58). This reaction was run at 0° C. for one hour. The mixture was warmed to room temperature, a 30 mole excess of EDA-Fl was added, and the reaction was run at room temperature with stirring overnight. The mixture was diluted to ten milliliters with 0.1M sodium phosphate (pH 7.0) and dialyzed in 2000 MWCO tubing against the dilution buffer. Dialysis was continued against distilled water and was followed by lyophilization to yield TNB-PGA/EDA-Fl conjugate (7.8 mg; $5.6 \times 10^{-7}$ mole).

The TNB group was removed by dissolving the TNB-PGA/EDA-Fl (7.8 mg) in 0.1M sodium phosphate (3.0 ml; pH 7.0) and treating with a 100 mole excess of 1,4-dithiothreitol for one hour at 40° C. The reaction was monitored for a shift of a 334 nm to a 412 nm peak on a UV/VIS spectrophotometer. The material was diluted to ten milliliters with distilled water and dialyzed in 2000 MWCO tubing against distilled water. Upon lyophilization, thiopropyl-PGA/EDA-Fl (HS-PGA/EDA-Fl; 8.4 mg) was obtained. At this point, a UV/VIS scan was taken to determine the number of fluoresceins per PGA molecule (i.e., loading). A value of 0.81 fluoresceins per PGA was calculated for this preparation.

Antibody activation: The monoclonal antibody, an anti-CEA antibody was maleimide activated per the method of Tuskada, et al. (JNCI: 73; 721–729, 1984) with the following exceptions. The antibody concentration was one mg/ml, and a 150 mole excess of N-succinimidyl m-(N-maleimido) benzoate (SMBE, MW 314.3; Sigma) was used. It was determined experimentally that a 150 mole excess was necessary to introduce between three and five maleimide groups to the anti-CEA antibody. Clean-up was performed using the Meares, et al. centrifuge method (Analytical Biochemistry: 1142; 68–78, 1984) with Sephadex G-50/80 (Sigma) in three milliliter syringe columns. The number of maleimides per antibody was determined using the titration method of Liu, et al., (Biochemistry: 18; 690–696, 1979). It was found that 4.6 maleimides were introduced per antibody during this antibody activation.

The thiopropyl-fluorescein-labeled PGA was then reacted with the maleimide derived antibody to yield the antibody/

PGA conjugate appropriate for a carcinoembryonic antigen ion-capture immunoassay. The maleimide-activated antibody (1.0 mg; 6.25×10$^{-9}$ mole) in 0.1M sodium phosphate (1.0 to 2.0 ml; pH 7.0) was pH adjusted to 6.5 with 1.0 N HCl. Then, a 10 mole excess of HS-PGA/EDA-Fl (approximately 1.0 mg) in 0.1M sodium phosphate (100 µl) was added to the activated antibody preparation. The conjugation was run overnight with gentle stirring at room temperature. The mixture was diluted to ten milliliters in 0.1M sodium phosphate (pH 7.0) and dialyzed in 50,000 MWCO tubing against 0.001M Na phosphate (pH 7.0) followed by lyophilization. The dry material was redissolved in distilled water (0.25 ml) and high performance liquid chromatography (HPLC) fractionated for the largest peak at A280. The chromatography was performed using a Bio-Sil TSK250 (Bio-Rad Laboratories, Richmond, Calif.) 300 mm×7.5 mm column, eluted at one milliliter/minute with 50 mM sodium sulfate, 20 mM sodium phosphate, and 0.3M NaCl (pH 6.8).

The largest peak was assayed for protein content using Bio-Rad's Bradford assay with a bovine IgG standard. The peak contained 95.5 µg/ml protein equating to 5.97×10$^{-7}$ molar protein (IgG MW 160,000). By scanning the UV/VIS and taking the absorbance at 494 nm, it was determined that this fraction also contained 2.12×10$^{-6}$ molar fluorescein, corresponding to 3.6 fluoresceins per antibody molecule. Knowing that there were 0.81 fluoresceins per PGA molecule, this equated to 4.4 PGA molecules conjugated to each antibody. The peak fraction was frozen and subsequently used in the assay.

An important aspect of the above described chemistries is that there exists but a single site of attachment between each polymeric anion and the antibody. A solitary covalent link between the two circumvents the potential intermolecular and intramolecular crosslinking that could occur if a polymeric anion having multiple activated groups were employed.

As an alternative to the above capture reagent example, a cationic derived antibody could also be formed for use in conjunction with an anionic solid phase material.

b. Preparation of the Solid Phase

The solid phase fibrous matrix of a disposable flow-through material was coated with a polymeric quaternary compound to give the solid phase a positive charge. Celquat® L-200 polymeric compound, a water soluble cellulose derivative, was used. A 1% aqueous solution of Celquat® L-200 polymeric compound (50 µl) was applied to the solid phase material, followed by a wash of diluent containing 300 mM NaCl, 50 mM Tris and 0.1% NaN$_3$ (75 µl; pH 7.5).

c. Preparation of the Indicator Reagent

The indicator reagent consisted of a conjugate of alkaline phosphatase and anti-CEA antibody fragment, which binds to a different epitope than the antibody specified in the capture reagent. The alkaline phosphatase-labeled anti-CEA antibody fragment was in a buffer containing: 50 mM Tris, 50 mM NaCl, 1.0 mM MgCl$_2$, 0.1 mM ZnCl$_2$, 5.0 mM sodium tartrate, 0.5% calf skin gelatin, and 3% mouse serum.

d. Immunoassay Protocol—Determination of CEA

The indicator reagent (70 µl) was placed into a reaction well. Then, buffered capture reagent (20 µl of anti-CEA/PGA conjugate in a buffer of 50 mM Na$_2$SO$_4$, 20 mM sodium phosphate, and 300 mM NaCl at pH 6.8) was added to the well. A 35 µl specimen containing CEA was added to the well, and the homogeneous immunoreaction mixture was incubated for 20 minutes at 34.5° C. Four different specimens were run in the assay, each of which was a CEA calibrator from the Abbott Laboratories CEA enzyme immunoassay kit. An aliquot of each reaction mixture (100 µl) was then applied to the solid phase material, followed by three 75 µl washes of diluent. Finally, an enzyme substrate (70 µl; 1.2 mM 4-methylumbelliferyl-phosphate in a solution of 100 mM AMP, 1.0 mM MgCl$_2$, 0.1% NaN$_3$, and 4.0 mM tetramisole at pH 10.3) was added at 34.5° C. for reaction with the indicator reagent, and the resulting rate of fluorescence was measured. The dose-response results of the assay are shown in Table 1. The results demonstrate that as the CEA test sample concentration increased there was a corresponding increase in the formation of capture reagent/analyte/indicator reagent complex, and therefore, the amount of detectable label associated with the solid phase increased.

TABLE 1

CEA Ion-capture Sandwich Assay Capture reagent: anti-CEA antibody-PGA conjugate Indicator reagent: alkaline phosphatase-labeled anti-CEA antibody fragment

| CEA (ng/ml) | Rate (counts/sec/sec) |
|---|---|
| 0 | 37 |
| 4 | 170 |
| 30 | 931 |
| 80 | 2398 |

Example 2

Competitive Inhibition Assay of Mouse Immunoglobulin a. Preparation of an IgG-PGA Capture Reagent A protein-A affinity purified mouse monoclonal immunoglobulin G was coupled to negatively charged PGA using a water-soluble carbodiimide reagent (1-ethyl-3-(3-dimethylamino-propyl) carbodiimide; EDCI) according to the following procedures.

Fluorescein-labeled PGA (10 mg; Fl-PGA) was added to an ice-cold solution of the antibody (4.8 mg/ml) in phosphate-buffered saline (PBS; 75 mM KH$_2$PO$_4$ and 300 mM NaCl at pH 7.2). To that solution was added a freshly prepared ice-cold solution of EDCI (100 µl; 10 mg/ml), and the resultant reaction mixture was allowed to warm to room temperature with continuous stirring for 2.5 hours. An additional freshly prepared ice-cold solution of EDCI (50 µl; 100 mg/ml) was then added to the reaction mixture with rapid stirring. The reaction mixture was stirred for another 1.5 hours. The mixture was then fractionated by gel filtration chromatography using a Spherogel TSK-3000SWG column (2.15 cm×30 cm) fitted with a Spherogel TSK-G guard column (2.15 cm×7.5 cm; Beckman Instruments, Inc., Fullerton, Calif., 92634). The column was eluted with PBS at a flow rate of five milliliters/minute. The PGA/antibody ratio of these pools was determined by quantitating the fluorescence in the Fl-PGA conjugates of the antibody. The results are shown in Table 2.

TABLE 2

Mouse IgG-PGA conjugates prepared using EDCI

| Pool | Peak Molecular Weight | PGA/antibody |
|---|---|---|
| I | 420,000 | 3.8 |
| II | 280,000 | 4.1 |

TABLE 2-continued

| Mouse IgG-PGA conjugates prepared using EDCl | | |
|---|---|---|
| Pool | Peak Molecular Weight | PGA/antibody |
| III | 220,000 | 5.5 | b. Preparation of the Solid Phase

A porous fibrous matrix material was coated with a polymeric quaternary ammonium compound (GAFQuat™ 755N quaternary ammonium compound; GAF Corporation) to form the solid phase. An aqueous solution of 0.5% GAFQuat™ quaternary ammonium compound (50 µl) was applied to the surface of the material, followed by a water wash (75 µl).

c. Binding of the Indicator Reagent to the Capture Reagent

The indicator reagent, an alkaline phosphatase conjugate of sheep anti-mouse immunoglobulin (Jackson ImmunoResearch Laboratories, Inc.; West Grove, Pa., 19390), was diluted in Tris-buffered saline containing 1% fish gelatin [25 mM Tris (hydroxymethyl) aminomethane and 100 mM NaCl, pH 7.5]. The capture reagent of PGA/mouse monoclonal antibody conjugate (Pool I of Table 2) was similarly treated. Two hundred microliters of each reagent was added to a series of test tubes which were then incubated at 37° C. for 30 minutes. An aliquot of the reaction mixture (75 µl) was applied to the solid phase, immediately followed by three 150 µl washes of Tris-buffered saline. Finally, an enzyme substrate (70 µl of 1.2 mM 4-methylumbelliferylphosphate in a solution of 100 mM AMP, 1 mM $MgCl_2$, 0.1% $NaN_3$, and 4 mM tetramisole; pH 10.3) was added to the materials at 32.7° C., and the resulting rate of fluorescence was measured. The results of the experiment are summarized in Tables 3 and 4.

TABLE 3

| Dose response of capture reagent/indicator reagent binding | |
|---|---|
| PGA/antibody* (µg/ml) | Rate of fluorescence (counts/sec/sec) |
| 10 | 1559 |
| 1 | 816 |
| 0.1 | 179 |
| 0.01 | 70 |
| 0 | 36 |

*The initial concentrations of PGA-coupled-antibody before mixing with a 1000-fold diluted alkaline phosphatase-labeled sheep anti-mouse immunoglobulin.

TABLE 4

| Dose response of indicator reagent/capture reagent* binding | |
|---|---|
| Indicator reagent titer** | Rate of fluorescence (counts/sec/sec) |
| $10^2$ | 5062 |
| $10^3$ | 796 |
| $10^4$ | 93 |
| $10^5$ | 10 |
| $10^6$ | 5 |

*The initial concentration of PGA-coupled-antibody before mixing with alkaline phosphatase-labeled sheep anti-mouse immunoglobulin was five µg/ml.
**The indicator reagent titer is the reciprocal of the dilution of the reagent stock.

d. Competitive Inhibition Assay for Mouse IgG

The capture reagent and indicator reagent were prepared as described above. All of the reagents were diluted in Tris-buffered saline containing 1% fish gelatin. The indicator reagent was diluted 1000-fold from the stock solution, and the capture reagent was diluted to ten µg/ml. In a series of test tubes, 150 µl each of appropriately diluted indicator reagent, capture reagent, and mouse monoclonal antibody were mixed. The mixtures were incubated at 37° C. for 30 minutes. Aliquots of the mixtures (75 µl) were applied to the solid phase, immediately followed by three 150 µl washes of Tris-buffered saline. An enzyme substrate (70 µl of 1.2 mM 4-methylumbelliferylphosphate in a solution of 100 mM AMP, 1 mM $MgCl_2$, 0.1% $NaN_3$, and 4.0 mM tetramisole; pH 10.3) was then added to the solid phase at 32.7° C., and the resulting rate of fluorescence was measured. The results of this example illustrating a competitive inhibition assay for mouse IgG are shown in Table 5. The results demonstrate that as the mouse monoclonal antibody concentration increased there was a corresponding decrease in the formation of capture reagent/indicator reagent complex, and therefore, the amount of detectable label associated with the solid phase decreased.

TABLE 5

| Inhibition of indicator reagent binding due to mouse monoclonal antibody Capture reagent: PGA/mouse monoclonal IgG conjugate Indicator reagent: alkaline phosphatase-sheep anti-mouse immunoglobulin conjugate | |
|---|---|
| Mouse IgG (µg/ml) | Rate of fluorescence (counts/sec/sec) |
| 0 | 110 |
| $3.3 \times 10^{-3}$ | 106 |
| $3.3 \times 10^{-2}$ | 98 |
| $3.3 \times 10^{-1}$ | 67 |
| 3.3 | 36 |
| 33 | 10 |

Example 3

Sandwich Assay for Human Chorionic Gonadotropin (hCG)

a. Preparation of the Capture Reagent

A highly negatively charged albumin derivative was prepared and coupled to anti-hCG antibodies to form the capture reagent according to the following procedures.

Modification of rabbit serum albumin to form a negatively charged protein derivative: Rabbit serum albumin (RSA) was extensively succinylated and coupled with para-azobenzenesulfonate by the procedure of Jou, et al., (Methods in Enzymology: Vol. 92, Part E; 257–276, Academic Press, 1983). Two per cent RSA in phosphate-buffered saline (PBS, 14 ml, pH 8.0) was mixed with 5% succinic annhydride in para-dioxane (2.28 ml). The pH was maintained at 8 by the addition of 1.0N NaOH. The reaction mixture was stirred at room temperature for 30 minutes. Hydroxylamine hydrochloride was added (0.6 g) and the pH of the solution was adjusted to 9.5 by adding an appropriate amount of 5N NaOH. The mixture was then dialyzed against water. The resultant $SUC_{65}$-RSA was coupled to para-azobenzenesulfonate according to the following reactions.

A suspension of para-azobenzenesulfonic acid (0.15 mmole, 26 mg) in 1N HCl (0.8 ml) was cooled in an ice bath and treated with 1N $NaNO_2$ (0.2 ml) for 30 minutes with rapid stirring. The resultant diazonium salt solution was added by drops to the ice cooled $SUC_{65}$-RSA solution with rapid stirring. The pH of the reaction mixture was maintained at 11 by the addition of 1.0N NaOH. The dark red reaction mixture was stirred and allowed to warm to room temperature for one hour before it was extensively dialyzed against water. The resultant Sp-SUC$_{65}$-RSA anionic derivatized protein was kept refrigerated until used.

Preparation of anti-hCG F(ab')$_2$ fragments: Anti-hCG F(ab')$_2$ fragments were prepared according to the method of Nisonoff, et al., (Arch. Biochem. Biophy.: 89; 230– 244, 1960) from affinity purified goat anti-hCG antibodies. A portion of affinity purified antibody solution in phosphate buffered saline (pH 7.2) was acidified to pH 4 by adding acetic acid. The preferred concentration of antibodies at this point was one mg/ml. Pepsin was added to reach a final concentration of 20 µg/ml. The mixture was incubated at 37° C. overnight. The reaction was stopped by adding 6.0N NaOH to bring the reaction mixture to a pH of 7.5. The digested antibody fragments solution was concentrated to 20 mg/ml. The F(ab')$_2$ fragments were purified by gel-filtration high performance liquid chromatography using a Spherogel TSK-3000SWG column (2.15 cm×30 cm) fitted with a Spherogel TSK-G guard column (2.15 cm×7.5 cm).

Preparation of anti-hCG TNB-Fab' fragments: Anti-hCG Fab' fragments were prepared and derivatized into a thiol-reactive form according to a modification of the methods of Parham, et al., (J. Immunol. Method.: 53: 133–173, 1982) and Brennan, et al., (Science: 229: 81–83, 1985). With stirring, a solution (158 µl) of 0.1M NaAsO$_2$ containing 20 mM EDTA was added to 1.28 ml of goat F(ab')$_2$ (goat anti-human chorionic gonadotropin antibody fragment, 16 mg/ml) containing trace $^{125}$I-F(ab')$_2$ in PBS. The reductive cleavage reaction was started by adding 0.1M cysteine-HCl (158 µl). The reaction mixture was overlayed with nitrogen and incubated with stirring at 37° C. for one hour. The reaction was then quenched by adding 19 mg of 5,5'-dithiobis-(2-nitrobenzoic acid). After stirring overnight at room temperature, the mixture was chromatographed on a PD-10 column (Pharmacia Inc., Piscataway, N.J.) preequilibrated with PBS, and then chromatographed on a size exclusion high performance liquid chromatography column [Spherogel TSK-2000SWG column (2.15 cm×30 cm) fitted with a Spherogel TSK-G guard column (2.15 cm×7.5 cm)]. The purified thionitrobenzoate derivative of Fab' (TNB-Fab') was concentrated to 7.9 mg/ml using a CX-10 ultra-filtration unit (Millipore Corp., Bedford, Ma.).

Coupling of anti-hCG TNB-Fab' fragments to Sp-SUC$_{65}$-RSA: A solution of 1M dithiothreitol (DTT; 86 µl) was added to a solution (4.2 ml) containing Sp-SUC$_{65}$-RSA (2.2 mg/ml) in 37.5 mM sodium phosphate, 150 mM NaCl, and 2.0 mM EDTA (pH 6.8). The mixture was incubated at 37° C. for three hours and then at room temperature overnight. The resulting reaction mixture was chromatographed on a 2.5 cm×20 cm column packed with Sephadex™ G-25 (Pharmacia Inc.) and preequilibrated with 75 mM sodium phosphate, 300 mM NaCl, and 2.0 mM EDTA (pH 6.8). A two milliliter portion of the pooled fractions of reduced Sp-SUC$_{65}$-RSA (0.48 mg/ml) was mixed with anti-hCG TNB-Fab' (0.15 ml; 7.9 mg/ml). The mixture was stirred at room temperature overnight. The reaction mixture was then treated with 100 mM iodoacetic acid (107 µl) and stirred for one hour at room temperature. The Fab'-Sp-SUC$_{65}$-RSA conjugate was purified by size exclusion high performance liquid chromatography using a Spherogel TSK-3000SWG column (2.15 cm× 30 cm) fitted with a Spherogel TSK-G guard column (2.15 cm×7.5 cm).

Coupling of anti-hCG antibodies to Sp-SUC$_{65}$-RSA: A solution (27 µl) of 30 mM succinimidyl 4-(N-maleimidomethyl)-cyclohexane-1-carboxylate in N,N-dimethylformamide was added to 2.25 ml of affinity purified goat anti-hCG antibody (3 mg/ml) in PBS. The resulting reaction mixture was stirred for one hour at room temperature and then chromatographed on a PD-10 column preequilibrated with 75 mM sodium phosphate, 300 mM NaCl, and 2.0 mM EDTA (pH 6.8). A 1.8 ml portion of the pooled fractions of modified antibodies (1.6 mg/ml) was mixed with three milliliters of the DTT-reduced Sp-SUC$_{65}$-RSA (0.48 mg/ml). After stirring at room temperature overnight, the reaction was quenched by adding 100 mM iodoacetic acid (0.25 ml) and stirring at room temperature for one hour. The antibody-Sp-SUC$_{65}$-RSA conjugate was purified by size exclusion high performance liquid chromatography in the manner described above.

b. Preparation of the Indicator Reagent

The indicator reagent consisted of an alkaline phosphatase-goat anti-hCG antibody conjugate (prepared by coupling anti-hCG antibody to periodate activated alkaline phosphatase) in an assay buffer containing 25 mM Tris (hydroxymethyl) aminomethane, 100 mM NaCl, 1 mM MgCl$_2$, 0.1 mM ZnCl$_2$, 0.07% NaN$_3$, and 1% fish gelatin at pH 7.5.

c. Sandwich Immunoassay Protocol for hCG

The ion-capture immunoassay protocol included the use of a solid phase prepared substantially in accordance with the method described in Example 2, the indicator reagent (alkaline phosphatase-goat anti-hCG antibody conjugate), one of two different capture reagents (goat anti-hCG Fab'-Sp-SUC$_{65}$-RSA and goat anti-hCG IgG-Sp-SUC$_{65}$-RSA) as prepared in Example 3.a. above, and a purified hCG standard solution. All reagents were appropriately diluted (as determined by a titer curve) in the assay buffer. Equal volumes (750 µl) of the indicator reagent and hCG sample solution were placed in a series of test tubes. After incubation at 37° C. for 30 minutes, a 125 µl aliquot of each incubated mixture was mixed in a separate tube with an equal volume of a capture reagent. The resulting mixtures were incubated for 30 minutes. The assay mixture (75 µl) was then added to each solid phase material. The solid phase materials were then washed three times with 150 µl amounts of washing buffer [25 mM Tris (hydroxymethyl) aminomethane, 100 mM NaCl, 1.0 mM MgCl$_2$, 0.1 mM ZnCl$_2$, and 0.07% NaN$_3$ at pH 7.5]. An enzyme substrate (70 µl of 1.2 mM 4-methylumbelliferylphosphate in a solution of 100 mM AMP, 1.0 mM MgCl$_2$, 0.1% NaN$_3$, and 4.0 mM tetramisole at pH 10.3) was then added to the solid phase materials. The resulting rate of fluorescence was measured at 32.7° C. The results of the experiment are summarized in Table 6. The results demonstrate that as the hCG test sample concentration increased there was a corresponding increase in the formation of capture reagent/analyte/indicator reagent complex, and therefore, the amount of detectable label associated with the solid phase increased.

TABLE 6 hCG Ion-capture
Sandwich Assay Comparing Different Capture Reagents
Indicator reagent: hCG-specific goat IgG-alkaline phosphatase

| | Rate of fluorescence (counts/sec/sec) hCG-specific capture reagents | |
|---|---|---|
| hCG (mIU/ml) | Goat IgG-Sp-SUC$_{65}$-RSA | Goat Fab'-Sp-SUC$_{65}$-RSA |
| 0 | 63 | 64 |
| 12.5 | 96 | 110 |
| 25 | 121 | 134 |
| 50 | 146 | 166 |
| 100 | 182 | 212 |

Example 4

Indirect Sandwich Ion-Capture Immunoassay for hCG

The indirect ion-capture immunoassay included the use of a solid phase prepared substantially as described in Example 2 above, an indicator reagent of alkaline phosphatase-sheep anti-mouse IgG conjugate (Jackson immunoResearch Laboratories, Inc.), a capture reagent of goat anti-hCG F(ab')$_2$-Sp-SUC$_{65}$-RSA as prepared in Example 3, an ancillary specific binding member of mouse monoclonal anti-hCG antibodies (ImmunoSearch; Thomas River, N.J., 08753), and a purified hCG standard solution. The ancillary specific binding member was used to bind with the analyte and the indicator reagent. All reagents were appropriately diluted in the assay buffer. Equal volumes (150 µl) of the indicator reagent, hCG sample solution, and ancillary specific binding member were placed in a series of test tubes. After incubation at 37° C. for five minutes, a 150 µl portion of capture reagent was added to each tube. The resulting mixtures were incubated for five minutes. The assay mixture (200 µl) was then added to each prepared solid phase material. The solid phase materials were then washed with washing buffer and treated with an enzyme substrate solution in the same manner as described in Example 3. above. The resulting rate of fluorescence was measured at 32.7° C. The results of the assay are summarized in Table 7. The results demonstrate that as the hCG test sample concentration increased there was a corresponding increase in the formation of capture reagent/analyte/ancillary specific binding member/indicator reagent complex, and therefore, the amount of detectable label associated with the solid phase increased.

TABLE 7

Ion-capture Indirect Sandwich Assay for hCG Capture reagent: goat anti-hCG F(ab')$_2$-Sp-SUC$_{65}$-RSA Indicator reagent: sheep anti-mouse IgG-alkaline phosphatase Ancillary specific binding member: mouse monoclonal anti-hCG antibody

| hCG (mIU/ml) | Rate of fluorescence (counts/sec/sec) |
|---|---|
| 0 | 13 |
| 1.5 | 18 |
| 3.3 | 27 |
| 6.3 | 40 |
| 12.6 | 70 |
| 25.0 | 112 |
| 50.0 | 230 |
| 100.0 | 443 |
| 200.0 | 732 |

Example 5

Indirect Sandwich Ion-Capture Immunoassay for hCG Using Two Ancillary Specific Binding Members The ion-capture immunoassay protocol included the use of a solid phase prepared substantially in accordance with the method described in Example 2, an indicator reagent of alkaline phosphatase-sheep anti-mouse IgG conjugate (Jackson ImmunoResearch Laboratories, Inc.), an ancillary specific binding member of mouse monoclonal anti-hCG antibodies (ImmunoSearch; Thomas River, N.J., 08753), and a purified hCG standard solution. Additionally, the protocol used a second ancillary specific binding member of affinity purified goat anti-hCG antibodies and a capture reagent of rabbit anti-goat IgG-Sp-SUC$_{65}$-RSA. The capture reagent was prepared by coupling affinity purified rabbit anti-goat IgG (Cappel; Cochranville, Pa., 19330) to Sp-SUC$_{65}$-RSA according to the procedure described in Example 3 above. All reagents were appropriately diluted in the assay buffer. Equal volumes (100 µl) of the indicator reagent, hCG sample solution, and first ancillary specific binding member were placed in a series of test tubes. After incubation (37° C. for ten minutes) the second ancillary specific binding member (100 µl) was added and the incubation was continued (at 37° C. for an additional five minutes). Finally, capture reagent (100 µl) was added to each tube. The resulting mixtures were incubated for five minutes. The assay mixture (200 µl) was then added to each prepared solid phase material. The solid phase materials were then washed with washing buffer, treated with enzyme substrate solution, and measured for the rate of fluorescence in the same manner as described in Example 3, above. The results of the assay are summarized in Table 8. The results demonstrate that as the hCG test sample concentration increased there was a corresponding increase in the formation of capture reagent/ancillary specific binding member/analyte/ancillary specific binding member/indicator reagent complex, and therefore, the amount of detectable label associated with the solid phase increased.

TABLE 8

Ion-capture Indirect Sandwich Assay for hCG
Capture reagent: rabbit anti-goat IgG-Sp-SUC$_{65}$-RSA
Indicator reagent: sheep anti-mouse IgG-alkaline phosphatase
Ancillary specific binding member:
mouse monoclonal anti-hCG antibody
Ancillary specific binding member: goat anti-hCG antibodies

| | Rate of Fluorescence (counts/sec/sec) | |
|---|---|---|
| Goat anti-hCG (ng/ml) | hCG (40 mIU/ml) | Negative Control (0 mIU/ml) |
| 250 | 3499 | 36 |
| 150 | 3708 | 34 |
| 50 | 3543 | 33 |
| 25 | 3155 | 30 |

Example 6

Ion-Capture Immunoassay for Anti-Progesterone Antibody a. Preparation of PGA-Labeled Goat Anti-Mouse Capture Reagent The following sequence of steps describes the chemistry employed for the preparation of an antibody/polyglutamic acid conjugate.

Conversion of PGA-sodium salt to the free acid form: The sodium salt of PGA (200 mg; $1.47 \times 10^{-5}$ mole; average MW 13,600; Sigma) was stirred with a cation exchange resin (AG50W-X8; 13 grams; Bio-Rad, Richmond, Calif.) in 60 milliliters of water for three hours. The supernatent was decanted, filtered, and evaporated providing an 80% yield of the free acid form of PGA as a white powder (137 mg; average MW 11,620).

Preparation of isothiocyanate-PGA (ITC-PGA): To a solution of the free acid form of PGA (65 mg; $5.6 \times 10^{-6}$ mole) in dimethylformamide (DMF; 2 ml) was added triethylamine (100 µl; $7.2 \times 10^{-4}$ mole) and 1,4-phenylenediisothiocyanate (110 mg; $5.7 \times 10^{-4}$ mole; Aldrich Chemical Company, Milwaukee, Wis.). After stirring overnight at room temperature, acetic acid (100 µl; $1.7 \times 10^{-3}$ mole) was added, and the reaction mixture was then evaporated. Methylene chloride (25 ml) was added to the residue, and after stirring for two hours the mixture was filtered to yield the ITC-PGA as a white powder (101 mg).

The ITC-PGA (295 µg; $2.5\times10^{-8}$ mole; in 40 µl of 20% DMF/0.1M sodium phosphate at pH 7.0) was added to a buffered solution of goat anti-mouse IgG (200 µg; $1.25\times10^{-9}$ mole; Sigma; in 40 µl of 0.1M sodium phosphate at pH 7) to form the PGA-labeled goat anti-mouse capture reagent. After stirring at room temperature for two days, 0.1M Tris (20 µl; pH 7.4) was added and the resulting mixture was stored at 2° to 8° C. until used.

b. Immunoassay for Anti-Progesterone Antibody

The anti-progesterone antibody ion-capture immunoassay included the use of solid phase materials coated with a polymeric quaternary compound as described in Example 1. A 60 µl sample was added to a reaction well. The samples consisted of a monoclonal anti-progesterone antibody at concentrations of 0, 5, 50, 100, 250, and 500 ng/ml in phosphate-buffered saline (PBS; 50 mM sodium phosphate, 99 mM NaCl, 0.1% $NaN_3$, at pH 7.4). Next, 20 µl of PBS were added to the reaction well, followed by 20 µl of the buffered indicator reagent, progesterone labeled with alkaline phosphatase (3 µg/ml in a Tris buffer of 50 mM Tris, pH 7.4, 150 mM NaCl, 1% $NaN_3$, 1 mM $MgCl_2$, 0.1 mM $ZnCl_2$, and 1% BSA). After incubating the mixture at 34.5° C. for ten minutes, the capture reagent was added (20 µl; PGA-labeled goat anti-mouse antibody at a 1/100 dilution in PBS of the stock solution described above). The mixture was then incubated an additional ten minutes at 34.5° C. A 100 µl aliquot of the mixture was then applied to the solid phase material, followed by three 75 µl washes of diluent. Lastly, the enzyme substrate solution (70 µl; 1.2 mM 4-methylumbelliferylphosphate in a solution of 100 mM AMP, 1 mM $MgCl_2$, 0.1% $NaN_3$, and 4.0 mM tetramisole at pH 10.3) was added to the solid phase, and the resulting rate of fluorescence was measured. The results of the assay are shown in Table 9. The results demonstrate that as the anti-progesterone antibody test sample concentration increased there was a corresponding increase in the formation of capture reagent/analyte/indicator reagent complex, and therefore, the amount of detectable label associated with the solid phase increased.

TABLE 9

Ion-capture Assay
for Mouse Monoclonal Anti-progesterone Antibody
Capture reagent: PGA-labeled goat anti-mouse antibody
Indicator reagent: alkaline phosphatase-labeled progesterone

| Anti-progesterone (ng/ml) | Rate of fluorescence (counts/sec/sec) |
| --- | --- |
| 0 | 9 |
| 5 | 31 |
| 50 | 254 |
| 100 | 441 |
| 250 | 1191 |
| 500 | 2721 |

Example 7

Indirect Competitive Ion-capture Immunoassay for Progesterone

The solid phase was prepared substantially in accordance with the method described in Example 1. A 60 µl sample of various concentrations of progesterone in PBS was mixed with 20 µl of progesterone-labeled alkaline phosphatase indicator reagent (0.4 µg/ml in the Tris buffer of Example 4) and 20 µl of mouse anti-progesterone antibody as an ancillary specific binding member (0.3 µg/ml in PBS). After incubating the mixture at 34.5° C. for ten minutes, 20 µl of the PGA-labeled goat anti-mouse antibody capture reagent were added as described in Example 6, above. The resulting mixture was incubated an additional ten minutes at 34.5° C. A 100 µl aliquot of the mixture was then applied to the solid phase material, followed by three washes of diluent. Lastly, the enzyme substrate solution (70 µl; 1.2 mM 4-methylumbelliferylphosphate in a solution of 100 mM AMP, 1 mM $MgCl_2$, 0.1% $NaN_3$, and 4.0 mM tetramisole at pH 10.3) was added to the solid phase, and the resulting rate of fluorescence was measured. The results of the assay are shown in Table 10. The results demonstrate that as the progesterone test sample concentration increased there was a corresponding decrease in the formation of capture reagent/ancillary specific binding member/indicator reagent complex, and therefore, the amount of detectable label associated with the solid phase decreased.

TABLE 10

Ion-capture Indirect Competitive Assay for Progesterone
Capture reagent: PGA-labeled goat anti-mouse antibody
Indicator reagent: alkaline phosphatase-labeled progesterone
Ancillary specific binding member:
mouse anti-progesterone antibody

| Progesterone (ng/ml) | Rate of fluorescence (counts/sec/sec) |
| --- | --- |
| 0 | 1203 |
| 1.88 | 277 |
| 3.75 | 145 |
| 7.5 | 67 |
| 15 | 30 |
| 30 | 16 |

Example 8

Activation of Poly-L-Glutamic Acid for the Formation of Anionic Capture Reagents The following sequence of steps describes the chemistry used for the bulk preparation of protein-PGA conjugates for the formation of negatively charged capture reagents.

a. Conversion of PGA-Sodium Salt to the Free Acid Form

The sodium salt of PGA (100 mg; $7.35\times10^{-6}$ mole; average MW 13,600; Sigma) was stirred overnight with a hydrogen form cation exchange resin (50 equivalents/glutamate residue; AG50W-X8; Bio-Rad). The resin previously had been swelled and washed in distilled water, and finally resuspended in distilled water (20 ml/7 gms dry weight of beads.) The supernatent was removed and lyophilized providing a 90% yield of the free acid form of PGA (PGAFA) as a white powder (80 mg; average MW 11,620). The free acid form was used to obtain solubility in organic solvents b. Preparation of ITC-PGAFA The PGAFA was dissolved in solvent (DMF at ten milligrams/milliliter.) A proton absorbing reagent (4-methyl morpholine) was added to the solution in the amount of about one equivalent per titratable free carboxylic acid. Next, about a 100 mole excess of an amine-reactive modification reagent (1,4-phenylene diisothiocyanate [DITC] in sufficient DMF to dissolve it) was added to the solution. The reaction mixture was stirred at room temperature overnight. The reaction mixture was rotavaporated to near dryness, and methylene chloride (25 ml) was added to precipitate the ITC-PGAFA. The flocculant precipitate was centrifuged, and the methylene chloride and unreacted DITC were removed. The precipitation/centrifugation process was repeated until substantially no detectable DITC remained. The DITC was detected using thin layer chromatography on silica slides developed in methylene chloride; ITC-PGAFA remains at the origin, DITC moves with the solvent front. The remaining solid was vacuum dried to yield the ITC-PGAFA as a yellow powder.

c. Coupling of ITC-PGAFA to Protein to Make Capture Reagents

The ITC-PGAFA (at about a 1 to about a 20 mole excess to the protein) was dissolved in 0.2M sodium phosphate buffer at pH 8.5, with the volume held as low as possible. The pH was adjusted to 8.5 as necessary. The desired protein was added to this solution and incubated overnight at 37° C. The preparations were then fractionated using HPLC on either an analytical TSK 400 Bio-Rad column (7.5×300 mm, at a 1 ml/min flow rate) for 1–2 milligram protein preparations, or a TSK 4000 Beckman column (31.5×300 mm, at a 5 ml/min flow rate) for 2–10 milligram protein preparations. The elution buffer contained 0.1M sodium phosphate and 0.3M NaCl at pH 6.8. Fractions were tested and appropriately combined. The amino acid content was determined for those fractions containing protein so that the coupling efficiency for the various proteins at various coupling ratios could be determined. The results of the determinations are presented in Table 11.

TABLE 11

Coupling Efficiencies of ITC-PGAFA with Various Proteins

| Protein | PGA Molar Excess | PGA Chain Number | Percent Substitution |
| --- | --- | --- | --- |
| Anti-CEA antibody | 1 | 0.77 | 77 |
| monoclonal 1.0 mg | 5 | 1.7 | 34 |
| | 10 | 3.1 | 31 |
| | 20 | 8.6 | 43 |
| Goat anti-rabbit antibody | 5 | 1.8 | 37 |
| monoclonal 1.0 mg | | | |
| Anti-β-hCG antibody | 10 | 4.6 | 46 |
| monoclonal 1.0 mg | 15 | 5.2 | 36 |
| monoclonal 10 mg | 15 | 7.8 | 52 |
| Anti-digoxin antibody | | | |
| monoclonal 1.0 mg | 15 | 8.1 | 54 |
| monoclonal 5.0 mg | 15 | 5.5 | 37 |
| Goat anti-mouse antibody | 15 | 4.3 | 29 |
| polyclonal 1.0 mg | | | |
| Anti-T4 antibody | 15 | 6.9 | 46 |
| monoclonal 1.0 mg | | | |
| Anti-T4 antibody | 15 | 13.8 | 92 |
| polyclonal 7.0 mg | | | |
| Rabbit Serum Albumin loaded with Theophylline | 15 | 7.8 | 52 |

Column 1 of Table 11 lists the quantity of protein used in the reactions to form the various capture reagents. Column 2 lists the mole excess of activated ITC-PGAFA that was reacted with the Column 1 protein. Column 3 provides the number of PGA chains attached per antibody by the reaction, calculated by amino acid analysis based upon a 40,000 average MW and 305 repeating glutamate residues. Column 4 provides a calculation of the percent efficiency of PGA chain substitution based upon the mole excess of activated PGA used in the reaction.

Example 9

Theophylline Ion-Capture Competitive Assay: Antigen Capture Format a. Preparation of Theophylline Capture Reagent The activation of theophylline was accomplished by dissolving theophylline-butyrate (10 mg; MW 280.29; 3.57× $10^{-5}$ moles) in methylene chloride (3.0 ml). A three mole excess of dicyclohexylcarbodiimide (22 mg; MW 206.3) and a three mole excess of N-hydroxysuccinimide (12.3 mg; MW 115.09) were added, and the reaction mixture was stirred overnight at room temperature. The mixture was filtered to remove dicyclohexylurea and was rotavaporated to dryness to yield ten milligrams of N-succinimidyltheophylline-butyrate(theophylline-butyrate-oSu).

The free acid of polyglutamic acid ($NH_2$-PGAFA; 1.4 mg; MW 11,798; 1.19×$10^{-7}$ moles) was dissolved in DMF (0.5 ml) and NMM (1.1 mg; MW 101.15; 1.07×$10^{-5}$ moles) The theophylline-butyrate-oSu (10 mg; at 1 mg/0.5 ml DMF) was added, and the reaction mixture was stirred overnight at room temperature. Unbound theophylline was removed by dialysis against a 0.1M Na phosphate buffer at pH 7.0. The theophylline content of the resulting capture reagent was analyzed, and the results demonstrated that 3.9 theophylline molecules were attached per PGA chain. The theophylline-PGA capture reagent, which was capable of binding with anti-theophylline antibody, was then diluted to 3 μg/ml in an assay buffer containing 25 mM Tris, 100 mM NaCl, 1 mM $MgCl_2$, 0.1 mM $ZnCl_2$, 0.1% $NaN_3$, and 1% fish gelatin at pH 7.2.

b. Preparation of the Solid Phase

A fiber matrix was coated with a polymeric quaternary compound to provide the solid phase with a positive charge. Celquat® L-200 polymeric compound, a water soluble cellulose derivative, was used. A 0.5% aqueous solution of Celquat® L-200 polymeric compound (50 μl) containing 10 mM NaCl (50 μl) was applied to the solid phase material.

c. Preparation of the Indicator Reagent

The indicator reagent consisted of a conjugate of alkaline phosphatase and anti-theophylline antibody, made substantially in accordance with the protocol described in Example 3.b. The indicator reagent was appropriately diluted (as determined by titer curve) in the assay buffer to give 0.17 micrograms of antibody/milliliter.

d. Immunoassay Protocol

The indicator reagent (200 μl) was placed within a series of reaction tubes. A theophylline standard solution (200 μl; theophylline-butyrate diluted to 0.6, 1.2, 2.5, 4.9, 9.9, 99.2, and 992 μg/ml in 50 mM Tris, 300 mM NaCl and 0.1% $NaN_3$ at pH 7.2) was then added to each tube. The mixture was incubated ten minutes at 37° C. Capture reagent (200 μl) was added to each tube, and the reaction mixtures were incubated ten minutes at 37° C. An aliquot of each reaction mixture (200 μl) was applied to the solid phase material, followed by one wash with diluent (75 μl). An enzyme substrate (70 μl; 1.2 mM 4-methylumbelliferyl-phosphate in a solution of 100 mM AMP, 1.0 mM $MgCl_2$, 0.1% $NaN_3$, and 4.0 mM tetramisole at pH 10.3) was added at 32° C. for reaction with the indicator reagent, and the resulting rate of fluorescence was measured. The results of the assay are shown in Table 12. The results demonstrate that as the theophylline analog test sample concentration increased there was a corresponding decrease in the formation of capture reagent/indicator reagent complex, and therefore, the amount of detectable label associated with the solid phase decreased.

TABLE 12

Theophylline Ion-Capture Competitive Assay:
Antigen Capture Format
Capture reagent: theophylline-PGA
Indicator reagent:
alkaline phosphatase-labeled anti-theophylline antibody

| Theophylline Analog (ng/ml) | Rate of fluorescence (counts/sec/sec) |
| --- | --- |
| 0 | 255 |
| 0.6 | 250 |
| 1.2 | 212 |
| 2.5 | 202 |
| 4.9 | 196 |
| 9.9 | 168 |
| 99.2 | 68 |
| 992 | 16 |

Example 10

Phenylcyclidine Ion-Capture Competitive Assay-Antigen Capture Format a. Preparation of Phenylcyclidine Capture Reagent 4,Hydroxy-Phenylcyclidine (1.1 mg; MW 259.37; $4.24 \times 10^{-6}$ moles) was dissolved in tetrahydrofuran (THF; 0.5 ml). One-half milliliter of 10% phosgene in benzene was added (130 mole excess.) The reaction was allowed to proceed at room temperature for 2.5 hours. The solvent was evaporated under a stream of nitrogen to yield a residue of phenylcyclidine-4-chloroformate.

The phenylcyclidine-4-chloroformate (1.1 mg) was dissolved in THF (0.5 ml). To this was added $NH_2$-PGAFA (1.7 mg; MW 11,798; $1.19 \times 10^{-7}$ moles) dissolved in 1-methyl-2-pyrrolidinone (0.5 ml). The reaction was carried out overnight at room temperature and then rotavaporated to dryness. The product was dissolved in 0.1M sodium phosphate (1.5 ml, pH 7.0). The precipitate was filtered, and the cloudy aqueous filtrate was extracted with methylene chloride until clear. The phenylcyclidine-PGA capture reagent, which was capable of binding with anti-phenylcyclidine antibody, was then diluted to 5 μg/ml in an assay buffer as described in Example 9.

b. Preparation of the Solid Phase

The solid phase was prepared substantially in accordance with the method described in Example 9.

c. Preparation of the Indicator Reagent

The indicator reagent consisted of a conjugate of alkaline phosphatase and anti-phenylcyclidine antibody. The indicator reagent was diluted 1/250 in the assay buffer as described in Example 9.

d. Immunoassay Protocol

The indicator reagent (140 μl) was mixed with a series of samples (50 μl each) containing known amounts of phenylcyclidine (0.0, 25, 60, 120, 250 and 500 ng/ml prepared in human urine), and the mixtures were incubated for ten minutes at 32° C. The phenylcyclidine-PGA capture reagent (100 μl) was added, and the reaction mixtures were incubated for ten minutes. An aliquot of each reaction mixture (200 μl) was applied to a solid phase material. The solid phase was then washed, two times. An enzyme substrate (70 μl; as described in Example 9) was added, and the resulting rate of fluorescence was measured. The results of the assay are shown in Table 13. The results demonstrate that as the phenylcyclidine test sample concentration increased there was a corresponding decrease in the formation of capture reagent/indicator reagent complex, and therefore, the amount of detectable label associated with the solid phase decreased.

TABLE 13

Phenylcyclidine Ion-Capture Competitive Assay:
Antigen Capture Format
Capture reagent: phenylcyclidine-PGA
Indicator reagent:
alkaline phosphatase-labeled anti-phenylcyclidine antibody

| Phenylcyclidine (ng/ml) | Rate of fluorescence (counts/sec/sec.) |
| --- | --- |
| 0 | 570 |
| 25 | 133 |
| 60 | 60 |
| 120 | 33 |
| 250 | 18 |
| 500 | 9 |

Example 11

Digoxin Ion-Capture Competitive Assay: Antigen Capture Format a. Preparation of a Digoxin-IgG-PGA Capture Reagent The digoxin-IgG-PGA capture reagent was prepared substantially in accordance with the method described in Example 8. c., with the following procedural modifications. The ITC-PGA (5 mg; $1.25 \times 10^{-7}$ mole; in 1.0 ml of 0.1M sodium phosphate at pH 8.5) was added to a buffered solution of rabbit IgG-digoxin (1 mg; $6.25 \times 10^{-9}$ mole; in 1.4493 ml of 0.1M sodium phosphate and 0.3M NaCl at pH 8.5) to form the capture reagent. The solution was stirred and incubated overnight at 37° C. The preparation was then fractionated using HPLC on a BioSil 400 (Bio-Rad 300 mm×7.5 mm gel filtration column) and eluted at one milliliter/minute with 0.1M sodium phosphate and 0.3M NaCl at pH 6.8. The digoxin-IgG-PGA capture reagent, which was capable of binding with anti-digoxin antibody, was then diluted to 3 μg/ml in an assay buffer as described in Example 9.

b. Preparation of the Solid Phase

The solid phase was prepared substantially in accordance with the method described in Example 9.

c. Preparation of the Indicator Reagent

The indicator reagent consisted of a conjugate of alkaline phosphatase and mouse anti-digoxin antibody (ImmunoSearch; Emeryville, Calif. 94608). The indicator reagent was diluted to 33.3 ng/ml in the assay buffer as described in Example 9.

d. Immunoassay Protocol

The indicator reagent (200 μl) was mixed with a series of samples (200 μl) containing known amounts of digoxin (0.5, 1.0, 2.5, 5.0 and 50.0 ng/ml prepared in normal human serum). The mixtures were incubated for 15 minutes at 37° C. The digoxin-IgG-PGA capture reagent (200 μl) was added, and the reaction mixtures were incubated for 15 minutes. An aliquot of each reaction mixture (200 μl) was applied to the solid phase material, followed by a wash. An enzyme substrate (70 μ; as described in Example 9) was added, and the resulting rate of fluorescence was measured. The results of the assay are shown in Table 14. The results demonstrate that as the digoxin test sample concentration increased there was a corresponding decrease in the formation of capture reagent/indicator reagent complex, and therefore, the amount of detectable label associated with the solid phase decreased.

TABLE 14

Digoxin Ion-Capture Competitive Assay: Antigen Capture Format
Capture reagent: digoxin-IgG-PGA
Indicator reagent:
alkaline phosphatase-labeled anti-digoxin antibody

| Digoxin (ng/ml) | Rate of fluorescence (counts/sec/sec) |
| --- | --- |
| 0 | 115 |
| 0.5 | 101 |
| 1.0 | 91 |
| 2.5 | 74 |
| 5.0 | 60 |
| 50.0 | 14 |

Example 12

Digoxin Ion-Capture Competitive Assay: Antibody Capture Format a. Preparation of the Indicator Reagent The indicator reagent consisted of a conjugate of alkaline phosphatase and digoxin (ImmunoSearch). The indicator reagent was diluted to 1/100 in the assay buffer as described in Example 9.

b. Immunoassay Protocol

The anti-digoxin-PGA capture reagent (200 µl, prepared substantially in accordance with the protocol described in Example 8.c) was mixed with a series of samples (200 µl each) containing known amounts of digoxin as described in Example 11. The mixtures were incubated for 15 minutes at 37° C. The indicator reagent (200 µl) was added, and the reaction mixtures were incubated for 15 minutes. An aliquot of each reaction mixture (200 µl) was applied to the solid phase (prepared as described in Example 9), followed by a wash. An enzyme substrate (70 µl; as described in Example 9) was added, and the resulting rate of fluorescence was measured. The results of the assay are shown in Table 15. The results demonstrate that as the digoxin test sample concentration increased there was a corresponding decrease in the formation of capture reagent/indicator reagent complex, and therefore, the amount of detectable label associated with the solid phase decreased.

TABLE 15

Digoxin Ion-Capture Competitive Assay:
Antibody Capture Format
Capture reagent: anti-digoxin antibody-PGA
Indicator reagent: alkaline phosphatase-labeled digoxin

| Digoxin (ng/ml) | Rate of fluorescence (counts/sec/sec) |
| --- | --- |
| 0 | 85 |
| 0.5 | 68 |
| 1.0 | 48 |
| 2.5 | 23 |
| 5.0 | 10 |
| 50.0 | 1 |

Example 13

Alternative Ion-Capture Sandwich Assay for hCG a. Preparation of the Capture Reagent An anti-hCG antibody-PGA capture reagent was prepared substantially in accordance with the method described in Example 8.c. above.

b. Preparation of the Solid Phase

A fiber matrix was wetted with buffer (80 µl; containing 300 mM NaCl, 50 mM Tris and 0.1% $NaN_3$ at pH 7.5). The matrix was coated with a 0.5% aqueous solution of Celquat® L-200 polymeric compound (50 µl; containing 10 mM NaCl) followed by a second wash with buffer.

c. Preparation of the Indicator Reagent

The indicator reagent consisted of a conjugate of alkaline phosphatase and goat anti-hCG antibody (made substantially in accordance with the protocol described in Example 3.b). The indicator reagent was appropriately diluted (as determined by titer curve) in assay buffer containing 25 mM Tris, 100 mM NaCl, 1 mM $MgCl_2$, 0.1 mM $ZnCl_2$, 0.1% $NaN_3$, 5% goat serum and 1% fish gelatin at pH 7.2.

d. Immunoassay Protocol

The indicator reagent (140 µl) was mixed with a series of samples (50 µl) containing known amounts of hCG in normal human serum. The mixtures were incubated for 10 minutes at 31°–32° C. The anti-hCG antibody-PGA capture reagent (100 µl) was added, and the reaction mixtures were incubated for 10 minutes. An aliquot of each reaction mixture (200 µl) was applied to the solid phase material, followed by a wash. An enzyme substrate (70 µl; as described in Example 9) was added, and the resulting rate of fluorescence was measured. The results of the assay are shown in Table 16. The results demonstrate that as the hCG test sample concentration increased there was a corresponding increase in the formation of capture reagent/analyte/indicator reagent complex, and therefore, the amount of detectable label associated with the solid phase increased.

TABLE 16 hCG Ion-capture Sandwich Assay
Capture reagent: anti-hCG antibody-PGA
Indicator reagent: alkaline phosphatase-labeled anti-hCG antibody

| | Rate of fluorescence (counts/sec/sec) hCG-specific capture reagents |
| --- | --- |
| 0 | 22 |
| 8 | 38 |
| 40 | 116 |
| 100 | 236 |
| 550 | 644 |
| 200,000 | 2058 |

Example 14

Ion-Capture Flow-Through Device for a Two-Step hCG Assay a. Preparation of the Solid Phase Test sample application pads (glass fiber matrix) were treated with various concentrations of an aqueous solution of Merquat-100® polymeric ammonium compound, 100 mM Tris, 100 mM sodium chloride, 0.1% fish gelatin, 0.1% sucrose and 0.1% sodium azide. The application pads were allowed to dry, and the pads were overlaid upon a layer of absorbent material. Substantially the same procedure was used to prepare a flow-through solid phase device treated with Celquat® L-200 polymeric compound. Alternative devices were prepared by treating the application pad with Merquat-100® polymeric quaternary ammonium compound (a cationic homopolymer of dimethyldiallylammonium chloride, 0.5% in water) immediately before use.

b. Preparation of the Indicator Reagent

The indicator reagent was a conjugate of goat anti-β-hCG antibody and alkaline phosphatase, diluted in 1% Brij®-35 polyoxyethylene (23) lauryl ether (Sigma), 100 mM Tris, 500 mM NaCl, 1 mM $MgCl_2$, 0.1 mM $ZnCl_2$, 0.1% $NaN_3$ and 0.5% non-fat dry milk at pH 7.2. The indicator reagent was filtered through a 0.22 µm filter before use.

In alternative indicator reagent preparations, dextran sulfate (MW 5,000) or heparin was included as a nonspecific binding blocker. The blocker was used to enhance the signal-to-noise ratio by inhibiting the binding of the labeled antibody to non-analyte.

c. Preparation of the Capture Reagent

A monoclonal anti-β-hCG antibody-PGA capture reagent was prepared substantially in accordance with the method described in Example 8.c. above. Every five milliliters of the coupling reaction mixture was fractionated on a gel filtration chromatography column (2.4× 54 cm, at a 0.4 ml/minute flow rate). The elution buffer contained 0.1M sodium phosphate, 0.3M NaCl and 0.05% $NaN_3$, at pH 8.5. The polymeric anion/antibody conjugate was diluted with 25 mM Tris, 100 mM NaCl, 1 mM $MgCl_2$, 0.1 mM $ZnCl_2$, 0.1% $NaN_3$, 10% normal mouse serum and 1% fish gelatin at pH 7.2. The capture reagent was filtered through a 0.22 µm filter before use.

d. Immunoassay Protocol

The capture reagent (80 µl) was mixed with an equal volume of test sample containing a known amount of hCG in normal human serum. The mixture was incubated at approximately 31°–32° C. for approximately twelve minutes. The specific binding reaction resulted in the formation of a capture reagent/analyte complex.

Each reaction mixture (80 µl) was then applied to a flow-through device, followed by a wash with Tris buffered saline (75 µl). The indicator reagent (50 µl) was then applied to the solid phase device and incubated for twelve minutes. The device was then washed two times.

An enzyme substrate (70 µl; 1.2 mM 4-methylumbelliferyl-phosphate in a solution of 100 mM AMP, 0.01% EDTA, 0.1% $NaN_3$, and 4.0 mM tetramisole at pH 10.3) was added, and the resulting rate of fluorescence was measured. The results of the assay are shown in Tables 17–19. The results demonstrated that as the hCG test sample concentration increased there was a corresponding increase in the formation of capture reagent/analyte/indicator reagent complex, and therefore, the amount of detectable label associated with the solid phase increased. The results show that the signal to noise ratio is improved by including a nonspecific binding blocker in the indicator reagent. Furthermore, the results demonstrated that the cationic homopolymer of dimethyldiallylammonium chloride was a preferred polymeric cation for the preparation of the solid phase for use in two-step assays wherein the device is subjected to one or more washings, e.g., the Merquat-100® polymeric ammonium compound has a nitrogen content of about 10% (exclusive of counter ion), whereas the Celquat® H-100 polymeric compound has a nitrogen content of about 1% (exclusive of counter ion).

TABLE 17 hCG Ion-capture two-step Sandwich Assay
Indicator reagent: alkaline phosphatase-labeled anti-β-hCG
antibody (with and without nonspecific binding blocker)
Solid phase: coated with a cationic homopolymer
of dimethyldiallylammonium chloride immediately before use

| hCG (mIU/ml) | Rate of fluorescence (counts/sec/sec) | |
| --- | --- | --- |
| | 2% dextran sulfate | no blocker |
| 0 | 68 | 255 |

TABLE 17-continued hCG Ion-capture two-step Sandwich Assay
Indicator reagent: alkaline phosphatase-labeled anti-β-hCG
antibody (with and without nonspecific binding blocker)
Solid phase: coated with a cationic homopolymer
of dimethyldiallylammonium chloride immediately before use

| hCG (mIU/ml) | Rate of fluorescence (counts/sec/sec) | |
| --- | --- | --- |
| | 2% dextran sulfate | no blocker |
| 100 | 1028 | 1104 |

TABLE 18 hCG Ion-capture two-step Sandwich Assay
Indicator reagent:
alkaline phosphatase-labeled anti-β-hCG antibody (with blocker)
Solid phase: with varying cationic polymer concentration

| hCG (mIU/ml) | Rate of fluorescence (counts/sec/sec) Merquat-100 ® polymeric ammonium compound (% w/v) | | | | |
| --- | --- | --- | --- | --- | --- |
| | 0.02 | 0.04 | 0.2 | 0.4 | 0.6 |
| 0 | 34 | 31 | 26 | 30 | 39 |
| 100 | 514 | 578 | 627 | 661 | 647 |

TABLE 19 hCG Ion-capture two-step Sandwich Assay
Indicator reagent:
alkaline phosphatase-labeled anti-β-hCG antibody
Solid phase: with 0.125% Celquat ® H-100 polymeric compound

| hCG (mIU/ml) | Rate of fluorescence (counts/sec/sec) quantity of capture antibody (µg/test) | | |
| --- | --- | --- | --- |
| | 0.268 | 0.402 | 0.652 |
| 0 | 86 | 100 | 115 |
| 100 | 186 | 202 | 259 |

Example 15

Ion-capture Flow-Through Device for Thyroid Stimulating Hormone (TSH) Assay a. Preparation of the Solid Phase An application pad (glass fiber matrix) was treated with an aqueous solution of Merquat-100® polymeric ammonium compound substantially in accordance with the procedure described in Example 14.a. The pad was then overlaid upon a layer of absorbent material to complete the flow-through solid phase device.

b. Preparation of the Indicator Reagent

The indicator reagent was a conjugate of goat anti-β-hCG antibody and alkaline phosphatase, diluted in 1% Brij®-35 polyoxyethylene (23) lauryl ether, 1% fish gelatin, 100 mM Tris, 500 mM NaCl, 1 mM $MgCl_2$, 0.1 mM $ZnCl_2$, 0.1% $NaN_3$ and 0.5% non-fat dry milk at pH 7.2. The indicator reagent was filtered through a 0.22 µm filter before use. Dextran sulfate (0.5%, MW 5,000) was added as a nonspecific binding blocker.

c. Preparation of the Capture Reagent

The capture reagent was prepared by coupling a Protein A purified monoclonal anti-TSH antibody with carboxymethyl amylose (CMA; Polysciences, Inc., Warrington, Pa.). Coupling was performed using a water-soluble carbodiimide reagent (1-ethyl-3-(3-dimethylaminopropyl)carbodiimide; EDCI) substantially in accordance with the following procedure.

The coupling mixture contained an antibody solution (2 ml; 1 mg/ml in MES buffer [25 mM, 2-(N-Morpholino)ethanesulfonic acid] pH 5.5) and CMA (1.6 ml; 10 mg/ml in MES buffer). To the solution was added, with stirring, a freshly prepared EDCI solution (40 µl; 100 mg/ml in MES buffer). The reaction mixture was stirred at room temperature for 40 minutes. The reaction was quenched by adding a 25% glycine solution (67 µl), and the product was then fractionated by gel filtration chromatography using a TSK-gel G4000SW column (2.15 cm×30 cm) fitted with a TSK-guard column SW (2.15 cm×7.5 cm; Anspec Co., Ann Arbor, Mich.). The column was eluted with PBS (0.1M sodium phosphate, 0.3 M NaCl and 0.05% sodium azide, at pH 6.8). The purified Antibody/CMA capture reagent was diluted in a diluent containing 50 mM Tris, 300 mM NaCl, 1% bovine serum albumin, 2.5% fish gelatin and 0.1% NaN₃, at pH 7.5.

d. Immunoassay Protocol

The capture reagent (30 µl) and Tris buffered saline (100 µl; 500 mM Tris, 300 mM NaCl and 0.1% NaH₃) were mixed with a test sample (50 µl) containing a known amount of hCG in normal human serum. The reaction mixture was incubated at approximately 33°–34° C. for approximately ten minutes. The specific binding reaction resulted in the formation of a capture reagent/analyte complex.

An aliquot of each reaction mixture (140 µl) was applied to a solid phase device, followed by a wash with Tris buffered saline (150 µl). The indicator reagent (70 µl) was applied to the device and incubated for approximately ten minutes. The device was then washed two times with buffer (100 µl each). The enzyme substrate (70 µl; 1.2 mM 4-methylumbelliferyl-phosphate in a solution of 100 mM AMP, 0.01% EDTA, 0.1% NaN₃, and 4.0 mM tetramisole at pH 10.3) was added, and the resulting rate of fluorescence was measured.

The results of the assay are shown in Table 20. The results demonstrated that as the concentration of TSH in the test sample increased, there was a corresponding increase in the formation of capture reagent/analyte/indicator reagent complex. Therefore, the amount of detectable label associated with the solid phase increased as the concentration of analyte increased. The results also demonstrated that the combination of Merquat-100® polymeric ammonium compound with polyacrylic acid or with carboxymethylamylose provided a solid phase and capture reagents which were advantageously used in two-step assays wherein the device is subjected to one or more washings or manipulations.

TABLE 20

TSH Ion-capture Two-step Sandwich Assay
(using polyacrylic acid or carboxymethylamylose polyanions)

| TSH (mIU/ml) | Rate of fluorescence (counts/sec/sec) | |
| --- | --- | --- |
| | carboxymethylamylose | polyacrylic acid |
| 0 | 7.1 | 6.4 |
| 0.5 | 13.3 | 12.1 |
| 2.0 | 34.7 | 28.7 |
| 10.0 | 147.5 | 119.8 |
| 40.0 | 513.9 | 442.6 |
| 100.0 | 1121.6 | 995.5 | e. TSH Capturing Efficiency

Radioiodinated TSH was used in the assay protocol, as described in Example 15. d, to demonstrate the more efficient TSH capturing of CMA-coupled antibodies than that of polyaspartic- and polyglutamic-coupled antibodies. The coupling of antibodies to the polyanions was performed substantially in accordance with the method described above (Example 15.c.) After the rate of fluorescence was measured at the end of the assay protocol, the radioactivity of TSH captured on the solid phase material was also measured by means of a scintillation spectrometer (Auto-Logic, Abbott Laboratories, North Chicago, Ill.). The results of this procedure are demonstrated in Table 20 (a).

TABLE 20 (a)

| Polyanion-coupled anti-TSH antibody | Capture of Radiolabeled % TSH captured | Rate of fluorescence (counts/sec/sec) |
| --- | --- | --- |
| Carboxymethylamylose | 70 | 662 |

Example 16

Ion-capture Flow-Through Device for a One-Step hCG Assay a. Preparation of the Solid Phase A glass fiber matrix was treated with an aqueous solution of Merquat-100® polymeric ammonium compound substantially in accordance with the procedure described in Example 14. a, above. The pad was then overlaid upon a layer of absorbent material to complete the device.

b. Preparation of the Indicator Reagent

The indicator reagent was a goat anti-β-hCG antibody conjugated to alkaline phosphatase and diluted in 3,33% Brij®-35 polyoxyethylene (23) lauryl ether, 5 mM Tris, 1 mM MgCl₂, 0.1 mM ZnCl₂, 0.1% NaN₃ and 5% fish gelatin at pH 7.2. The indicator reagent was filtered through a 0.2 µm filter before use. In alternative indicator reagent preparations, carboxymethyl cellulose (MW 250,000) or carboxymethyl dextran was included as a nonspecific binding blocker.

c. Preparation of the Capture Reagent

A monoclonal anti-hCG antibody-PGA capture reagent was prepared substantially in accordance with the method described in Example 15. c, above. The polymeric anion/antibody conjugate was diluted with 3.33% Brij®-35 polyoxyethylene (23) lauryl ether, 5 mM Tris, 500 mM NaCl, 1 mM MgCl₂, 0.1 mM ZnCl₂, 0.1% NaN₃, and 5% fish gelatin at pH 7.2. The enzyme substrate was 1.2 mM 4-methylumbelliferyl-phosphate in a solution of 100 mM AMP, 0.01% EDTA, 0.1% NaN₃, and 4.0 mM tetramisole at pH 10.3.

d. Immunoassay Protocol

The capture reagent (50 µl), indicator reagent (55 µl) and sample diluent buffer (35 µl: 75% normal calf serum, 25% normal goat serum and 0.2% NaN₃, filtered through a 0.22 µm filter before use) were mixed with a test sample (30 µl) containing a known amount of hCG in normal human serum. The mixture was incubated at approximately 33°–34° C. for approximately fourteen minutes. The specific binding reaction resulted in the formation of a capture reagent/analyte/indicator reagent complex.

An aliquot of each reaction mixture (110 µl) was then applied to a solid phase device, followed by two washes with Tris buffered saline (75 µl). The enzyme substrate (65 µl) was added, and the resulting rate of fluorescence was measured.

The results of the assay are shown in Table 20. The results demonstrated that as the hCG test sample concentration increased there was a corresponding increase in the formation of capture reagent/analyte/indicator reagent complex, and therefore, the amount of detectable label associated with the solid phase increased. Furthermore, the results show that the signal to noise ratio was improved when a free polyanionic substance was included in the indicator reagent as a nonspecific binding blocker, even though the capture reagent was a polymeric anion/antibody conjugate.

TABLE 21 hCG Ion-capture Sandwich Assay
Indicator reagent: alkaline phosphatase-labeled anti-hCG antibody

| hCG (mIU/ml) | 0 | 0.01 | 0.25 | 0.5 |
|---|---|---|---|---|
| | Rate of fluorescence (counts/sec/sec) | | | |
| | % carboxymethyl cellulose in indicator reagent | | | |
| 0 | 37.2 | 23.8 | 17.2 | 13.3 |
| 10 | 76.8 | 58.4 | 48.8 | 42.1 |
| 1000 | 1803.6 | 1665.4 | 1692.2 | 1507.2 |
| | Rate of fluorescence (counts/sec/sec) | | | |
| | % carboxymethyl dextran in indicator reagent | | | |
| 0 | 35.6 | 30.0 | 17.8 | 14.8 |
| 10 | 75.2 | 68.4 | 54.7 | 49.8 |
| 1000 | 1826.6 | 1851.2 | 1739.5 | 1646.6 |

Example 17

Ion-Capture Test strip for an hCG Sandwich Assay a. Preparation of the Solid Phase A rectangular zone on a central portion of a strip of nitrocellulose (5 μm pore size; Schleicher & Schuell; Dassel, Germany) was treated with an aqueous solution of 0.05% Merquat-100® polymeric ammonium compound and 10 mM Tris to form a positively charged capture or detection zone.

b. Preparation of the Indicator Reagent

The indicator reagent was made of colloidal selenium particles coated with mouse monoclonal anti-hCG antibody. The indicator reagent was appropriately diluted (as determined by titer curve) in assay buffer containing 50 mM Tris, 2% lactose, 2% casein, 1% goat serum and 1% mouse serum at pH 8.4.

c. Preparation of the Capture Reagent

A goat anti-β-hCG antibody was coupled to poly-L-glutamic acid using 1-ethyl-3-( 3-dimethylaminopropyl)-carbodimide substantially in accordance with the method described in Example 15. c, above. The capture reagent was then appropriately diluted in the same diluent as the indicator reagent.

d. Immunoassay Protocol

The indicator reagent (50 μl) was mixed with an equal volume of capture reagent. The mixture was then combined with a series of samples (0, 50, 100 and 250 mIU/ml; 150 μl each) containing known amounts of hCG in normal human urine. The resultant reaction mixtures were incubated for five minutes at room temperature. The specific binding reaction resulted in the formation of a capture reagent/analyte/indicator reagent complex.

Each reaction mixture (250 μl) was then applied to one end of the prepared strip of nitrocellulose. The mixture was allowed to migrate through the strip to the capture zone and through the zone. Capture reagent and complexes thereof were retained at the capture zone, wherein the indicator reagent complexed with the retained capture reagent indicated the amount of analyte in the test sample as well as the presence of analyte in the test sample. The 0 mIU/ml test sample produced no coloration of the capture zone. The 50, 100 and 250 mIU/ml test samples produced visible coloration of the capture zone.

Example 18

Ion-Capture Test Strip Device for an hCG Assay a. Preparation of the Solid Phase A rectangular zone on a central portion of a strip of nitrocellulose (5 μm pore size; Schleicher & Schuell) was treated with an aqueous solution of 1% Celquat® L-200 polymeric compound to form a positively charged capture zone. The cationic polymer was dispensed using a #29 gauge tube (MICRO Inc., Elmhurst, N.Y.) moving at a rate of 0.5 inches/second with a flow rate of 0.05 milliliter/minute.

b. Preparation of the Indicator Reagent

The indicator reagent was made of colloidal selenium particles coated with mouse monoclonal anti-hCG antibody. The indicator reagent was appropriately diluted (as determined by titer curve) in assay buffer containing 50 mM Tris, 2% lactose, 2% casein, 1% goat serum and 1% mouse serum at pH 8.4.

c. Preparation of the Capture Reagent

An anti-β-hCG antibody was coupled with poly-glutamic acid substantially in accordance with the method described in Example 8.c, above.

d. Preparation of the Assay Device

A reagent pad or test sample application pad was prepared by soaking a pad of absorbant material (40 μpore glass fiber material; Lydall Inc., Hamptonville, N.C.) with a mixture containing the capture reagent (20 μg/ml) and the indicator reagent (antibody concentration 0,024 mg/mL, selenium concentration 0.3 mg/mL) in Tris buffered saline (0.1M Tris, 0.9% NaCl, pH 7.8), 1.0% casein. The pad was then air dried. The test strip device was then constructed by contacting the test sample application pad and nitrocellulose strip, and then double laminating the pad and nitrocellulose so that the application pad overlapped at least an end portion of the nitrocellulose strip offset from the capture zone.

e. Immunoassay Protocol

A test sample containing a known amount of hCG in normal human urine (0, 50 and 250 mIU/ml; 50 μl each) was applied to the test sample application pad of the assay device, or the application pad was dipped into the test sample. The test sample, resolubilized assay reagents and complexes thereof migrated from the application pad to and through the nitrocellulose strip. After five minutes, at room temperature, the specific binding reaction and the ion-capture reaction resulted in the formation of a capture reagent/analyte/indicator reagent complex which was immobilized at the capture zone of the test strip. Unbound indicator reagent and test sample components passed through the capture zone. The 0 mIU/ml test sample produced no detectable signal at the capture zone. The 50 mIU/ml test sample produced a faintly detectable visible signal at the capture zone. The 250 mIU/ml test sample produced a strongly detectable visible signal at the capture zone. The assay results also demonstrated that a homogeneous specific binding reaction could form a tertiary complex while reacting in a solid phase test strip device.

Example 19

Ion-Capture Test Strip Device for a Phenylcyclidine (PCP) Assay a. Preparation of the Solid Phase A rectangular zone on a central portion of an elongated strip of nitrocellulose (3 mm in width) was treated with an aqueous solution of 0.5% Merquat-100® polymeric ammonium compound to form a positively charged capture zone.

b. Preparation of the Indicator Reagent

The indicator reagent was made of colloidal selenium particles coated with PCP antibody.

c. Preparation of the Capture Reagent

A PCP antigen was conjugated to poly-glutamic acid substantially in accordance with the method described in Example 10. a, above.

d. Preparation of the Assay Device

An assay reagent pad (3 mm in width) or test sample application pad was prepared by soaking an absorbant material (Whatman PD075 glass fiber filter; Whatman Specialty Papers, Clifton, N.J.) with the indicator reagent (2.5 mg/ml; 4% casein, 4% sucrose, 1% polyethylene glycol [MW 15,000–25,000] in 0.01M Tris). The application pad was then air dried. The application pad and nitrocellulose where then assembled so that the reagent pad overlapped one end of the nitrocellulose by approximately one millimeter.

e. Immunoassay Protocol

The capture reagent (15 μl) and an equal volume of test sample, containing a known dilution of PCP in distilled water (1:10, 1:100, 1:1000, 1:10000), were mixed. The mixture was applied to the test sample application pad. The mixture was allowed to migrate through the pad and strip for at least ten five minutes. The competitive binding reaction resulted in the formation of capture reagent/indicator reagent complex and indicator reagent/analyte complex, wherein the amount of capture reagent/indicator reagent complex decreased as the amount of analyte in the test sample increased. The polyelectrolyte reaction resulted in the immobilization of the capture reagent/indicator reagent complex in the capture zone of the test strip. Unbound indicator reagent and unreacted test sample components, as well as indicator reagent/analyte complex, passed through the capture zone. The assay results demonstrated that the higher the amount of PCP in the test sample, the lower the detectable signal at the capture zone. The assay results also demonstrated that a homogeneous specific binding reaction could take place in a solid phase test strip device.

Example 20

Ion-Capture Flow-Through Device for an hCG Assay a. Preparation of the Solid Phase A glass fiber filter material was treated with an aqueous solution of 0.125% Celquat® L-200 polymeric quaternary ammonium compound to form a positively charged capture zone. The glass fiber filter was then set upon a second layer of absorbent material which serves to pick up excess reagents and test sample which pass through the layer containing the charged detection zone.

b. Preparation of the Indicator Reagent

The indicator reagent was made of colloidal gold particles coated with affinity purified goat anti-β-hCG antibody. A solution containing gold chloride (100 mg) in distilled water (51 0 ml) was heated to boiling and mixed with 1% sodium citrate (8.0 ml). The heat was removed when the color of the solution changed from yellow to dark red (approximately three minutes). The solution was cooled to room temperature by flushing under tap water. A portion (10 ml) of the resultant gold colloid was titrated with 150 millimolar borate buffer (pH 9.0) to pH 7.0.

Fifty microliters of goat anti-β-hCG antibody (9 mg/ml) was added to the gold colloid and mixed at room temperature for one minute. The mixture was then treated with 10% bovine serum albumin (300 μl) and centrifuged at 14,000 rpm for one minute. The bottom layer of the colloid/antibody mixture (approximately 320 μl) was recovered for use as the indicator reagent.

c. Preparation of the Capture Reagent

Purified monoclonal anti-hCG antibodies were modified with ITC-PGA substantially in accordance with the methods described in Examples 6 and 8, above.

d. Immunoassay Protocol

All reagents were appropriately diluted in an assay buffer containing 50 mM Tris, 150 mM NaCl, pH 7.5 and 3% casein. A test sample (50 μl) containing a known amount of hCG in normal human urine (0, 25, 50, 100 and 250 mlU/ml) was mixed with an equal volume of indicator reagent, and the mixture was incubated at room temperature for five minutes. Capture reagent (50 μl) was then added to the mixture. The resulting mixture was then transferred to the solid phase that had been pre-wetted with buffer (80 μl). The flow-through devices were then rinsed twice with buffer. A visible purple color was detected for those devices which received hCG-containing reaction mixtures, while the 0 mlU/ml test sample produced no detectable signal at the capture zone. The darkness of the signal at the capture zone increased with the increase of hCG concentration.

Example 21

Competitive Digoxin Assay Using Ion-Capture a. Preparation of the Solid Phase

Test sample application pads (glass fiber matrix) were overcoated with various concentrations of an aqueous solution of Merquat-100® polymeric ammonium compound, 100 mM Tris, 100 mM sodium chloride, 0.1% fish gelatin, 0.1% sucrose and 0.1% sodium azide. The application pads were allowed to dry and were then overlaid upon a layer of absorbent material to prepare flow-through devices.

b. Preparation of the Indicator Reagent

The indicator reagent was a conjugate of digoxin dialdehyde and alkaline phosphatase, diluted in 50 mM Tris, 100 mM NaCl, 1 mM $MgCl_2$, 0.1 mM $ZnCl_2$, 0.1% $NaN_3$ and 0.1% bovine serum albumin at pH 7.5.

c. Preparation of the Capture Reagent

The first capture reagent, a goat anti-digoxin antibody coupled to 1,4-phenylene diisothiocyanate activated poly-L-aspartic acid (ITC-PAA), was prepared substantially in accordance with the method described in Example 8.c, above. Poly-L-aspartic acid was used in place of poly-L-glutamic acid.

A second capture reagent was made of rabbit anti-goat IgG antibody coupled to poly-L-aspartic acid using EDCI substantially in accordance with the coupling protocol described in Example 15. c, above. An analyte-specific ancillary binding member (goat anti-digoxin antibody) was used together with this capture reagent to bind the analyte to the solid phase. In one embodiment, the capture reagent was a preformed complex of the negatively charged anti-goat antibody and the goat anti-digoxin antibody. Both the first and second capture reagents were appropriately diluted before use with 50 mM Tris, 50 mM NaCl, 0.1% $NaN_3$ and 0.1% bovine serum albumin at pH 7.5.

d. Immunoassay Protocol

In assays using the first capture reagent, or direct capture system, the capture reagent (60 μl) was mixed with test sample (18 μl) containing a known amount of digoxin. The reaction mixture was incubated at approximately 33°–34° C.

for about ten minutes. The specific binding reaction resulted in the formation of a capture reagent/analyte complex. The indicator reagent (60 µl) was then added to the reaction mixture, and the mixture was incubated for about another eleven minutes. The specific binding reaction resulted in the formation of capture reagent/indicator reagent complex in proportion to the amount of analyte present in the test sample. A portion of each reaction mixture (80 µl) was then applied to the solid phase, followed by two washes with Tris buffered saline (75 µl). An enzyme substrate (70 µl; 1.2 mM 4-methylumbelliferyl-phosphate in a solution of 100 mM AMP, 0.01% EDTA, 0.1% NaN$_3$, and 4.0 mM tetramisole at pH 10.3) was added, and the resulting rate of fluorescence was measured.

In an indirect assay using the second capture reagent, the preformed capture reagent/ancillary binding member complex (50 µl), indicator reagent (55 µl) and digoxin test sample (25 µl) were combined with sample diluent buffer (91 µl). The mixture was incubated for approximately nine minutes. The specific binding reaction resulted in the formation of capture reagent/ancillary binding member/analyte complex and capture reagent/ancillary binding member/indicator reagent complex in proportion to the amount of analyte present in the test sample. An aliquot of the reaction mixture (180 µl) was then applied to the solid phase, followed by two washes with Tris buffered saline (75 µl). The enzyme substrate (70 µl) was added, and the resulting rate of fluorescence was measured.

The results of the assay are shown in Table 22. The results demonstrated that as the digoxin test sample concentration increased there was a corresponding decrease in the formation of complex containing indicator reagent. Therefore, the amount of detectable label associated with the solid phase decreased with the increase of digoxin in the test sample.

of absorbent material to form the individual assay devices.

b. Preparation of the Indicator Reagent

The indicator reagent was a conjugate of T3 and alkaline phosphatase, diluted in 50 mM Tris, 100 mM NaCl, 1.0 mM MgCl$_2$, 0.1 mM ZnCl$_2$ and 1.0% bovine serum albumin at pH 7.5. Dextran sulfate (MW 5,000) was included as a nonspecific binding blocker. The blocker was used to enhance the signal-to-noise ratio by inhibiting the binding of the labeled antibody to non-analyte.

c. Preparation of the Capture Reagent

The capture reagent, an anti-T3 antibody coupled to polyaspartic acid (PAA-anti-T3 antibody), polyacrylic acid (PAcA-anti-T3 antibody) or carboxymethyl cellulose (CMA-anti-T 3 antibody) anionic polymer molecules, was prepared substantially in accordance with the method described in the Example 15. c EDCI coupling method, with the exception that no chromatographic filtration of the capture reagent was performed. The capture reagent was diluted with 800 mM Tris, 50 mM NaCl, 0.1% NaN$_3$, 0.01% furosemide, 0.1% Tween-20,1.0% bovine serum albumin and 0.08 mg/ml goat IgG at pH 7.4.

d. Immunoassay Protocol

The capture reagent (50 µl) was mixed with an equal volume of test sample, containing a known amount of Total T3, and sample diluent buffer (150 µl). The reaction mixture was incubated for approximately 15 minutes. The specific binding reaction resulted in the formation of a capture reagent/analyte complex.

Each reaction mixture (150 µl) was then applied to a solid phase. The indicator reagent (60 µl) was then applied to the solid phase and incubated for eight minutes. The device was then washed two times. An enzyme substrate (50 µl) was added, and the resulting rate of fluorescence was measured.

In an alternative assay format, the solid phase was also washed prior to the addition of the indicator reagent. In yet

TABLE 22

| | Digoxin Ion-capture Competitive Assay | |
|---|---|---|
| Concentration of Antibody/Test: Indicator Reagent: | 162 ng Goat anti-Digoxin Conjugate | 90 ng Rabbit anti-Goat/64 ng Goat anti-Digoxin Conjugate |
| | Rate of fluorescence (counts/sec/sec) | |
| Digoxin (ng/ml) | Direct | Indirect |
| 0 | 680 | 456 |
| 0.5 | 546 | 387 |
| 1 | 413 | 309 |
| 2 | 303 | 247 |
| 3 | 261 | 179 |
| 5 | 183 | 121 |

Example 22

Ion-capture Flow-Through Device for a Total T3 (Triiodothyronine) Competitive Assay a. Preparation of the Solid Phase Test sample application pads (glass fiber matrix) were treated with various concentrations of an aqueous solution of Celquat® L-200 polymeric quaternary ammonium compound or Merquat-100® polymeric ammonium compound, 100 mM Tris, 100 mM sodium chloride, 0.1% fish gelatin, 0.1% sucrose and 0.1% sodium azide. The application pads were allowed to dry, and the pads were overlaid upon a layer another assay format, the capture reagent and test sample were combined and incubated, followed by the addition of indicator reagent and further incubation prior to placing an aliquot of the reaction mixture on the solid phase.

The polyelectrolyte interaction of the capture reagent and the oppositely charged solid phase resulted in the immobilization of capture reagent and capture reagent complexes on the solid phase devices. An enzyme substrate (70 µl; 1.2 mM 4-methylumbelliferyl-phosphate in a solution of 100 mM AMP, 0.01% EDTA, 0.1% NaN$_3$, and 4.0 mM tetramisole at pH 10.3) was added, and the resulting rate of fluorescence was measured.

In each assay, the results demonstrated that as the Total T3 test sample concentration increased there was a corresponding increase in the formation of capture reagent/analyte complex, and therefore, the amount of detectable label associated with the solid phase decreased. Furthermore, the results show that the signal to noise ratio is improved by including a nonspecific binding blocker, dextran sulfate, in the indicator reagent.

TABLE 23

Total T3 Competitive Assay
Calibration data comparing one-step and two-step assay protocols

| (per test) Indicator Reagent: | (0.25 µg) no blocker | (0.02 µg) with 0.1% dextran sulfate |
|---|---|---|
| Calibrators concentration ng/ml total T3 | Rate of fluorescence (counts/sec/sec) | |
| 0 | 518 | 616 |
| 0.5 | 386 | 513 |
| 1.0 | 310 | 403 |
| 2.0 | 218 | 260 |
| 4.0 | 123 | 109 |
| 8.0 | 71 | 48 |

TABLE 24

Total T3 Competitive Two-Step Assay comparison
of indicator reagents with and without a nonspecific binding blocker

| (per test) Indicator Reagent: T3 alkaline phosphatase dilution: | antibody (0.02 µg) no blocker 1:400 | antibody (0.02 µg) with 0.1% dextran sulfate 1:150 |
|---|---|---|
| Calibrators concentration ng/ml total T3 | Rate of fluorescence (counts/sec/sec) | |
| 0 | 641 | 536 |
| 2.0 | 361 | 220 |
| 8.0 | 81 | 39 |

TABLE 25

Total T3 Competitive Assay
Calibration data comparing different T3 capture reagents

| (per test) | antibody (0.013 µg) | antibody (0.015 µg) | antibody (0.013 µg) |
|---|---|---|---|
| Calibrators concentration ng/ml total T3 | Rate of fluorescence (counts/sec/sec) | | |
| 0 | 509 | 544 | 507 |
| 0.5 | 401 | 443 | 394 |
| 1.0 | 332 | 344 | 322 |
| 2.0 | 203 | 219 | 204 |
| 4.0 | 94 | 107 | 99 |
| 8.0 | 47 | 57 | 51 |

Example 23

HIV-1 Anti-p24 Antibody Detection Using an Ion-Capture Sandwich Assay

The solid phase devices were prepared by overcoating glass fiber matrixes with a polycationic substance and overlaying the matrixes upon an absorbent material. The capture reagent, was prepared by the covalent coupling of a polyanionic substance to purified recombinant p24 antigen. The indicator reagent was a conjugate of alkaline phosphatase and anti-biotin antibody which bound to the analyte antibody by means of an analyte-specific ancillary specific binding member, i.e., biotinylated p24 antigen. The enzyme substrate was 4-methylumbelliferyl-phosphate.

The capture reagent was reacted with the test sample to form a capture reagent/analyte complex. Excess reagent and test sample components were removed and the complex was immobilized by passage through the oppositely charged solid phase. The amount of captured analyte was then determined by the sequential addition of the ancillary specific binding member, indicator reagent and enzyme substrate.

Example 24

Ion-Capture Device with Procedural Control

In an alternative embodiment, the solid phase reaction matrix of Example 17 was prepared such that two assay reagents were incorporated into the matrix in an overlapping design to form the detection zone. The reaction of one reagent completed one portion of a detectable pattern, and the reaction of a second reagent completed another portion of the detectable pattern.

For example, the anionic polymer (such as polyglutamic acid) was applied to the solid phase to form the vertical bar of a "cross" shaped design. The anionic polymer attracted and attached to the oppositely charged capture reagent comprising an analyte-specific binding member conjugated to a polymeric cation. The reaction of the capture reagent, analyte and an indicator reagent specific for the analyte resulted in a detectable complex being immobilized at the vertical bar.

A procedural control reaction zone, which did not involve an analyte reaction, was formed in the shape of the horizontal bar of the cross-shaped detection zone. A reagent which reacted with and immobilized the indicator reagent without the formation of an analyte-containing complex was used.

For example, when the indicator reagent was made of colloidal gold particles coated with affinity purified goat anti-β-hCG antibody, then the horizontal bar of the cross-shaped detection zone included a specific binding member which would directly bind to the goat anti-β-hCG antibody, e.g., a rabbit anti-goat antibody. Thus, detectable label was immobilized in the horizontal bar whether or not there was analyte present in the test sample.

It will be appreciated by one skilled-in-the-art that the concepts of the present invention are equally applicable to any separation techniques or homogeneous binding assays (wherein the signal generating ability of the label is not altered during the binding reaction) by using oppositely charged solid phase materials and capture reagents. The embodiments described in detail herein are intended as examples rather than as limitations of the polyelectrolyte reactions and assays. Thus, the description of the invention is not intended to limit the invention to the particular embodiments described, but it is intended to encompass all equivalents and subject matter within the spirit and scope of the invention as described above and as set forth in the following claims.

What is claimed is:

1. A method for determining the presence or amount of an analyte in a test sample, comprising the steps of:
   a) providing a test sample suspected of containing an analyte;
   b) forming a reaction mixture by contacting the test sample with a soluble capture reagent comprising a first binding member conjugated to a carboxymethylamylose polyanion and an indicator reagent comprising a labeled second binding member, wherein said first and second binding members specifically bind the analyte;
   c) incubating the reaction mixture under conditions sufficient for the analyte and reagents to react and form soluble capture reagent/analyte/indicator reagent complexes;
   d) after incubating, determining the presence or amount of analyte by
      (i) contacting the reaction mixture with a solid phase comprising a polymeric cation substance and having a pre-determined charge opposite to said carboxymethylamylose polyanion so that capture reagent/analyte/indicator reagent complexes and unreacted capture reagent are separated from the reaction mixture and coupled to the solid phase by the ionic attraction of the oppositely charged carboxymethylamylose polyanion and solid phase; and
      (ii) detecting label associated with the solid phase or with the unreacted indicator reagent in the reaction mixture.

2. The method according to claim 1, further comprising the addition of a non-specific binding blocker to said reaction mixture.

3. The method according to claim 2, wherein said non-specific binding blocker is a separate reagent or is contained within a member selected from the group consisting of said indicator reagent or said capture reagent.

4. The method according to claim 2, wherein said non-specific binding blocker is an unbound polymeric anion material.

5. The method according to claim 4, wherein said unbound polymeric anion material is selected from the group consisting of dextran sulfate, heparin, carboxymethyl dextran, carboxymethyl cellulose, pentosan polysulfate, inositol hexasulfate and β-cyclodextrin sulfate.

6. The method according to claim 1, wherein said polymeric cation substance has a nitrogen content of at least about two percent.

7. The method according to claim 1, wherein the indicator reagent comprises an unlabeled second binding member which specifically binds the analyte and a labeled third binding member which specifically binds the second binding member.

8. A method for determining the presence or amount of an analyte in a test sample, comprising the steps of:
   a) providing a test sample suspected of containing an analyte;
   b) forming a reaction mixture by contacting the test sample with a soluble capture reagent comprising a carboxymethylamylose polyanion conjugated to a first specific binding member which specifically binds the analyte;
   c) incubating the reaction mixture under conditions sufficient for the analyte and capture reagent to react and form soluble capture reagent/analyte complexes;
   d) after incubating, determining the presence or amount of analyte by
      (i) contacting the reaction mixture with a solid phase comprising a polymeric cation substance and having a pre-determined charge opposite to said carboxymethylamylose polyanion so that capture reagent/analyte complexes and unreacted capture reagent are separated from the reaction mixture and coupled to the solid phase by the ionic attraction of the oppositely charged carboxymethylamylose polyanion and solid phase;

(ii) contacting the solid phase with an indicator reagent comprising a detectable label conjugated to a second specific binding member which specifically binds the analyte;

(iii) incubating the solid phase and the indicator reagent under conditions sufficient for the analyte and reagents to react and form capture reagent/analyte/indicator reagent complexes; and (iv) detecting label associated with the solid phase or with the unreacted indicator reagent.

9. The method according to claim 8, further comprising the step of washing said solid phase prior to contacting said solid phase with said indicator reagent.

10. The method according to claim 8, further comprising the addition of a non-specific binding blocker to said reaction mixture.

11. A method for determining the presence or amount of an analyte in a test sample, comprising the steps of:

a) providing a test sample suspected of containing an analyte;

b) forming a reaction mixture by contacting the test sample with a soluble capture reagent comprising a carboxymethylamylose polyanion conjugated to a binding member which specifically binds the analyte and an indicator reagent comprising an analyte analog conjugated to a detectable label;

c) incubating the reaction mixture under conditions sufficient for the analyte and reagents to react and form soluble capture reagent/analyte or capture reagent/indicator reagent complexes;

d) after incubating, determining the presence or amount of analyte by (i) contacting the reaction mixture with a solid phase comprising a polymeric cation substance and having a pre-determined charge opposite to said carboxymethylamylose polyanion so that capture reagent/analyte or capture reagent/indicator reagent complexes and unreacted capture reagent are separated from the reaction mixture and coupled to the solid phase by the ionic attraction of the oppositely charged carboxymethylamylose polyanion and solid phase; and (ii) detecting label associated with the solid phase or with the unreacted indicator reagent in the reaction mixture.

* * * * *

UNITED STATES PATENT AND TRADEMARK OFFICE
CERTIFICATE OF CORRECTION

PATENT NO. : 5,459,080
DATED : October 17, 1995
INVENTOR(S) : Janina Adamczyk, et al It is certified that error appears in the above-indentified patent and that said Letters Patent is hereby corrected as shown below:

In column 5, line 51, "polymer" should be "polybrene". (first occurrence).

In column 8, line 7 "syncvial" should be "synovial".

In column 8, line 26 insert a space between the "a" and the "s" in "asteroid" so that it reads "a steroid".

In column 10, line 54 "H+NR3" should be "H+NR$_3$".

In column 13, lines 33 and 34 "-(2-pyridyldithio)propionate" should be "3-(2-pyridyldithio)propionate"

In column 13, lines 45-47 (Formula)

$$\text{"—(amino acid)}_2 \text{—C—R—"}\quad \overset{\overset{O}{\|}}{}$$

should be $$\text{"—(amino acid)}_n \text{—C—R—"}\quad \overset{\overset{O}{\|}}{}$$

In column 19, line 30 "polycional" should be "polyclonal".

In column 26, line 29 "I5" should be removed.

In column 29, line 54 "propionyI-PGA" should be "propionyl-PGA".

In column 30, line 44-45, "thiopropyI-PGA/EDA-FI" should be "thiopropyl-PGA/EDA-FI"

In column 37, line 9 "immunoResearch" should be "ImmunoResearch".

In column 13, line 49, before "the" should be --wherein--.

UNITED STATES PATENT AND TRADEMARK OFFICE
CERTIFICATE OF CORRECTION

PATENT NO. : 5,459,080                                      Page 2 of 4
DATED      : October 17, 1995
INVENTOR(S): Janina Adamczyk, et al It is certified that error appears in the above-indentified patent and that said Letters Patent is hereby corrected as shown below:

In column 46, Table 16, column titles "hCG (mIU/ml)" and "hCG-ITC-PGA" are missing.

In column 47 & 48, Table 17, "Capture reagent: anti-ß-hCG antibody-PGA (0.5 µg/test)" is missing as the second line of the heading.

Column 48, Table 18, "Capture reagent: anti-ß-hCG antibody-PGA (0.5 µg/test)" is missing as the second line of the heading.

Column 48, Table 19, "Capture reagent: anti-ß-hCG antibody-PGA" is missing as the second line of the heading.

Column 50, Table 20(a), should be as follows:

Table 20 (a)
Capture of Radiolabeled TSH in the Cationic Solid Phase Material

| Polyanion-coupled anti-TSH antibody | %TSH captured | Rate of fluorescence (counts/sec/sec) |
|---|---|---|
| Carboxymethylamylose | 70 | 662 |
| Polyaspartic Acid | 1.5 | 37 |
| Polyglutamic Acid | 2.0 | 57 |

Column 51, Table 21, refer to page 72 of original spec. "Capture reagent: anti hCG antibody-PGA" is missing from heading.

Column 52, Line 31 "0,024" should be "0.024".

UNITED STATES PATENT AND TRADEMARK OFFICE
CERTIFICATE OF CORRECTION

PATENT NO. : 5,459,080

DATED : October 17, 1995

INVENTOR(S) : Janina Adamczyk, et al

Page 3 of 4

It is certified that error appears in the above-indentified patent and that said Letters Patent is hereby corrected as shown below:

Column 55, Table 22, refer to page 79 of original spec. Add "Protocol:" and "Precoated Solid Phase:" as the first two title lines for column one. Add "Semi-sequential One-Step" and "0.2% Merquat-100®" as the first two title lines for column two. Add "One-Step" and "0.2% Merquat-100®" as the first two title lines for column three. Under the title words "Conjugate" in columns two and three, add the word "Direct" for column two and "Indirect" for column three.

Column 57, Table 23, add three lines of titles to each of the three columns: Add "Protocol:", "Precoated Solid Phase:", and "Capture Antibody:" as the first three lines of the titles of column one. Add "One-step", "0.5% Celquat®", and "ITC-PGA anti-T3 antibody" as the first three lines of the titles of column two. Add "Two-step", "0.2% Merquat-100®", and "EDAC-PAA anti-T3 antibody" as the first three lines of the titles of column three.

UNITED STATES PATENT AND TRADEMARK OFFICE
CERTIFICATE OF CORRECTION

PATENT NO. : 5,459,080
DATED : October 17, 1995
INVENTOR(S) : Janina Adamczyk, et al It is certified that error appears in the above-indentified patent and that said Letters Patent is hereby corrected as shown below:

Column 57, Table 24, add "Precoated Solid Phase" and "Capture Antibody:" as the first two lines of column one titles. Add "0.2% Merquat-100®" and "EDAC-PAA anti-T3" as the first two lines of column two titles. Add "0.2% Merquat-100®" and "EDAC-PAA anti-T3" as the first two lines of column three titles.

Column 57, Table 25, add "Capture Antibody:" as the first line of column one titles. Add "PAA-anti-T3" as the first line of column two titles. Add "PAcA-anti-T3" as the first line of column three titles. Add "CMA-anti-T3" as the first line of column four titles.

Signed and Sealed this

Fourth Day of June, 1996

*Attest:*

BRUCE LEHMAN

*Attesting Officer*  Commissioner of Patents and Trademarks